United States Patent [19]
Brown et al.

[11] Patent Number: 5,361,133
[45] Date of Patent: Nov. 1, 1994

[54] METHOD AND APPARATUS FOR ANALYZING FEET

[75] Inventors: Algie C. Brown, Atlanta; Carl T. Welty, Chamblee; Henry G. Williams, Roswell; David M. Williams, Dunwoody; James M. Dabbs, III, Duluth, all of Ga.

[73] Assignee: Footmark, Inc., Atlanta, Ga.

[21] Appl. No.: 903,017

[22] Filed: Jun. 23, 1992

[51] Int. Cl.$^5$ .............................................. G01B 11/24
[52] U.S. Cl. .................... 356/376; 33/3 R; 33/6; 33/515
[58] Field of Search ............... 356/372, 376, 379, 383, 356/384; 33/3; 12/146; 73/172, 765; 364/550, 558, 561

[56] References Cited

U.S. PATENT DOCUMENTS

| | | | |
|---|---|---|---|
| 2,043,187 | 6/1936 | Owens | 128/2 |
| 2,975,519 | 3/1961 | Berlin, Jr. et al. | 33/3 |
| 3,325,799 | 6/1967 | Farris | 340/279 |
| 3,328,882 | 7/1967 | Blivice | 33/3 |
| 3,457,647 | 7/1969 | Cohen et al. | 33/3 |
| 3,727,606 | 4/1973 | Sielaff | 128/25 |
| 3,926,177 | 12/1975 | Hardway, Jr. et al. | 128/25 |
| 4,134,063 | 1/1979 | Nicol et al. | 324/61 R |
| 4,169,462 | 10/1979 | Strubé | 128/721 |
| 4,267,728 | 5/1981 | Manley et al. | 73/172 |
| 4,294,014 | 10/1981 | Baumann et al. | 33/3 C |
| 4,381,788 | 5/1983 | Douglas | 128/722 |
| 4,437,138 | 3/1984 | Nicol | 361/283 |
| 4,538,353 | 9/1985 | Gardner | 33/3 C |
| 4,598,717 | 7/1986 | Pedotti | 128/779 |
| 4,604,807 | 8/1986 | Bock et al. | 33/3 C |
| 4,644,801 | 2/1987 | Kustanovich | 73/172 |
| 4,827,763 | 5/1989 | Bourland et al. | 73/172 |
| 4,858,621 | 8/1989 | Franks | 128/779 |
| 4,895,160 | 1/1990 | Reents | 128/671 |
| 5,025,476 | 6/1991 | Gould et al. | 356/374 |
| 5,128,880 | 7/1992 | White | 356/376 |
| 5,164,793 | 11/1992 | Wolfersberger et al. | 356/376 |

OTHER PUBLICATIONS

Alexander, Cheo, Johnson; The Assessment of Dynamic Foot-to-Ground Contact Forces and Plantar Pressure Distribution: A Review of the Evolution of Current Techniques and Clinical Applications; Foot & Ankle/vol. 11, No. 3 Dec. 1990.

Primary Examiner—Richard A. Rosenberger
Assistant Examiner—Hoa Q. Pham
Attorney, Agent, or Firm—Louis T. Isaf

[57] ABSTRACT

A method and apparatus for measuring feet for fitting shoes which utilizes matrixes of pressures sensors and optical sensors connected to a controller and a monitor. An apparatus of the invention includes a housing which houses a controller and a monitor and defines left and right foot wells for receiving left and right feet, respectively. The floor of each foot well includes a pressure pad assembly which includes a matrix of pressure sensor contacts covered by a variably resistive pressure pad to form pressure sensor matrixes. A digital signal processor normalizes and smooths the pressure data for display on the monitor. Infrared LED's and phototransistors are located around the perimeter of each foot well and are utilized to measure the length, width, and heights of a foot. A microprocessor addresses each LED and phototransistor separately. The controller reads data created by the DSP and IR microprocessor, calculates additional data, and displays the resulting data on the monitor. The pressure sensors and optical sensors are utilized to determine, among others, foot length, foot width, shoe size, foot volume, foot shape, force distribution, pronation, arch type, and recommended last type. Such determinations, along with intended use information obtained from the customer, are compared to a database of available shoes to determine recommended best fits for each customer. Such data can also be stored or transferred to an external system for storage with reference to each particular customer.

8 Claims, 21 Drawing Sheets

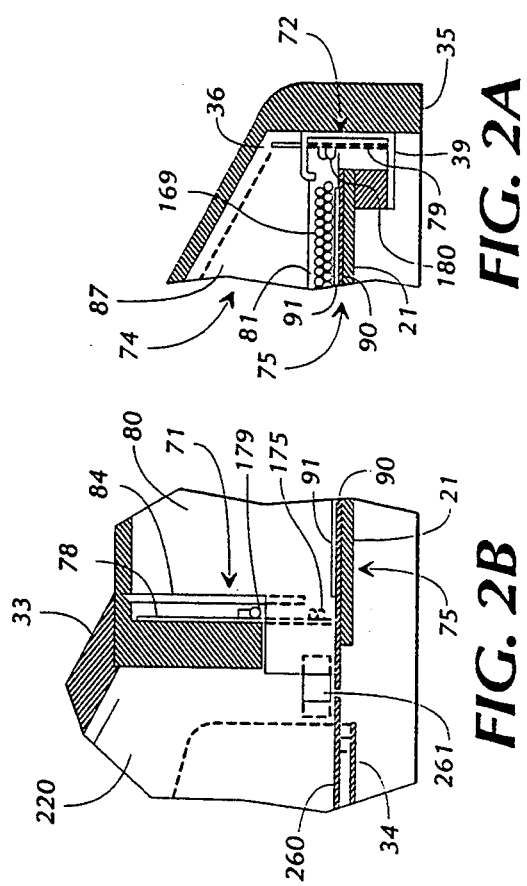
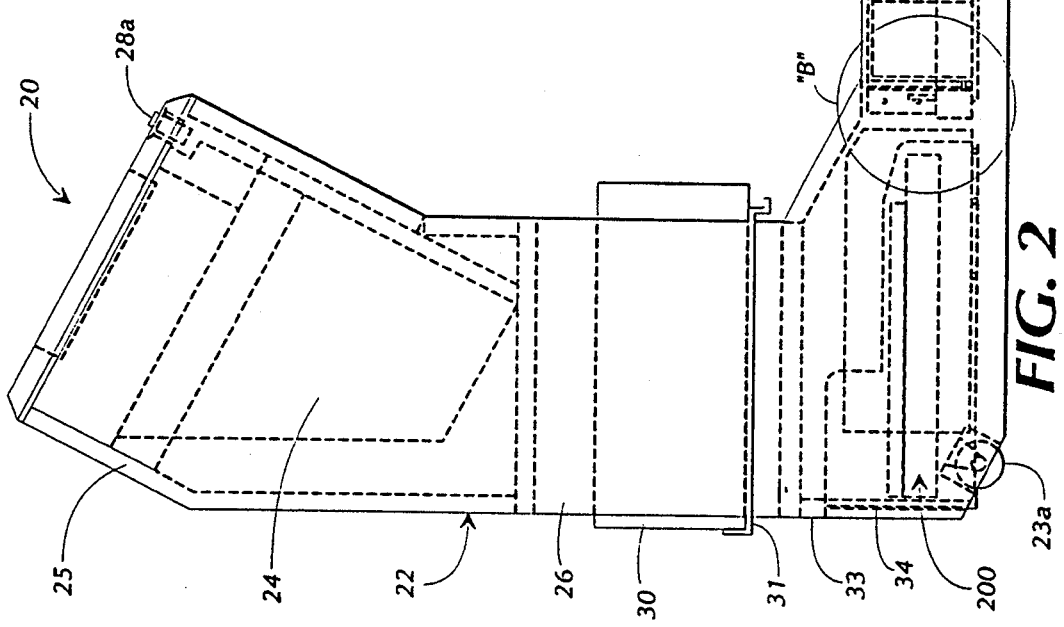

5,361,133

METHOD AND APPARATUS FOR ANALYZING FEET

FIELD OF THE INVENTION

This invention relates generally to the field of analyzing feet, and in its most preferred embodiments, to integrating pressure and optical sensors to measure feet for selecting shoes.

BACKGROUND OF THE INVENTION

It is well known that shoes and feet come in a variety of sizes and shapes. Consequently, in order to provide a particular consumer with a pair of shoes, a shoe retailer must determine that particular consumer's shoe size. If the consumer is unaware of his or her shoe size, the shoe retailer typically measures the consumer's feet to determine the appropriate shoe size. One of the most commonly used devices for measuring feet for fitting shoes is the Branach device. This manual device includes two levers slidably mounted upon a labeled platform for determining the length and width of a particular foot. Since shoes have traditionally been available in men, women, and children sizes, three different types of Branach devices, corresponding to each of these sizing schemes, have been utilized by shoe retailers. The manual nature of the Branach device, as well as the need for using three different devices for men, women, and children, suggest the need for a system which automatically measures all types of feet for fitting shoes.

Various types of automatic feet measuring devices have been developed in the past. Many of these devices utilize complex mechanical moving components which are subject to ordinary shortcomings of moving mechanical parts. Other devices include one or more light sources located to shine light onto the top or bottom of a foot to cast planar outlines of the foot onto light sensitive sensors which are monitored to produce foot length and width measurements. Although length and width measurements are useful and relatively easily obtained from such systems, additional desirable measurements which are difficult or impossible to obtain from such prior systems include, among others, foot height, foot volume, foot shape, and force distribution throughout the foot.

There is a need, therefore, in the industry for a method and an apparatus for measuring feet for fitting shoes which address these and other related, and unrelated, problems.

SUMMARY OF THE INVENTION

Briefly described, the present invention, includes a method and apparatus for analyzing feet and, in its most preferred embodiment, includes a method and apparatus for measuring feet for fitting shoes. An apparatus for accomplishing the inventive method includes a housing which houses a controller and a monitor and defines left and right foot wells for receiving left and right feet, respectively. The floor of each foot well includes a pressure pad assembly which includes a matrix of pressure sensor contacts covered by a variably resistive pressure pad to form a matrix of pressure sensors. Each pressure sensor is independently addressable and includes two contacts separated by an insulated gap which is selectively bridged by the pressure pad to effect an independently measurable, pressure-related resistance across the insulated gap.

A digital signal processor (DSP) is electrically positioned between the controller and the pressure sensors and controls operation of the pressure sensors. During operation, a reference voltage is driven onto one row at a time addressed through an analog multiplexer array. The resulting current flowing from one column addressed through a second analog multiplexer array is converted into an amplified analog voltage. Subsequently, the analog voltage is converted into a resulting digital representation. The DSP then references a table to convert the digital representation into pounds and thereafter transfers the raw pound data, one row at a time, to the controller through a first-in-first-out (FIFO) memory resource. The DSP also conditions each row of pound data for display on the monitor. A smoothing method and an auto-normalization method are also employed to provide more accurate and visually appealing monitor output screens.

Located around the inner perimeter of each foot well are optical sensors, consisting of infrared (IR) light emitting diodes (LED's) and corresponding phototransistors, which are utilized to measure the length, width, and heights of a foot. A microprocessor is electrically positioned between the controller and the optical sensors and controls operation of the optical sensors by addressing and driving the sensors through programmable array logic circuits (PAL's) and multiplexer arrays. According to the preferred method, one LED in each foot well is supplied a modulated current while a corresponding phototransistor is checked for receipt of the modulated signals.

Before a foot is placed in a foot well, the optical sensors operate in a scan mode which only checks every fifth LED/phototransistor pair. When a foot is placed in a foot well, thus blocking one of the optical sensors, the optical sensors enter into a tracking mode where the outer limits of the width, length, and height are tracked, thus saving time over repeatedly checking every optical sensor.

When the foot wells are empty, the controller displays on the monitor a slide show of user defined screens. When the optical sensors detect a foot and enter into the tracking mode, the controller reads data created by the DSP and IR microprocessor, calculates additional data, and displays the resulting data on the monitor. The pressure sensors and optical sensors are utilized to determine, among others, foot length, foot width, shoe size, foot volume, foot shape, force distribution, pronation, arch type, and recommended last type. Such determinations, along with intended use information obtained from the customer, are compared to a database of available shoes to determine recommended best fits for each customer. Such data can also be stored or transferred to an external system for storage with reference to each particular customer.

It is therefore an object of the present invention to provide a method and apparatus for analyzing feet for fitting shoes which includes pressure sensors and optical sensors.

Another object of the present invention is to provide an apparatus for fitting shoes which includes a left pressure pad assembly and a right pressure pad assembly, wherein each pressure pad assembly includes a matrix of independent pressure sensors which share a variably resistive pressure pad.

Another object of the present invention is to provide a method for displaying a visual representation of a pressure matrix which includes auto-normalization and smoothing.

Yet another object of the present invention is to provide an apparatus for fitting shoes which includes, for each foot, length, width, and height matrixes of optical emitters located on one side and end of a foot well and corresponding length, width, and height matrixes of optical receivers located on an opposing side and end of the foot well.

Still another object of the present invention is to provide a method of using optical sensors to efficiently track outer profile boundaries of a foot.

Still another object of the present invention is to provide a method of integrating foot pressure data and optical profile data to fit shoes.

Still another object of the present invention is to provide a method of comparing foot measurements to a database of shoes to recommend suitable shoes.

These and other objects, features and advantages of the present invention will become apparent upon reading and understanding this specification, taken in conjunction with the accompanying drawings.

BRIEF DESCRIPTION OF THE DRAWINGS

FIG. 2 is a left side view of the apparatus of FIG. 1.

FIG. 2(a) is a detailed view of the area "A" of FIG. 2.

FIG. 2(b) is a detailed view of the area "B" of FIG. 2.

DETAILED DESCRIPTION OF THE PREFERRED EMBODIMENT

Figure 1:
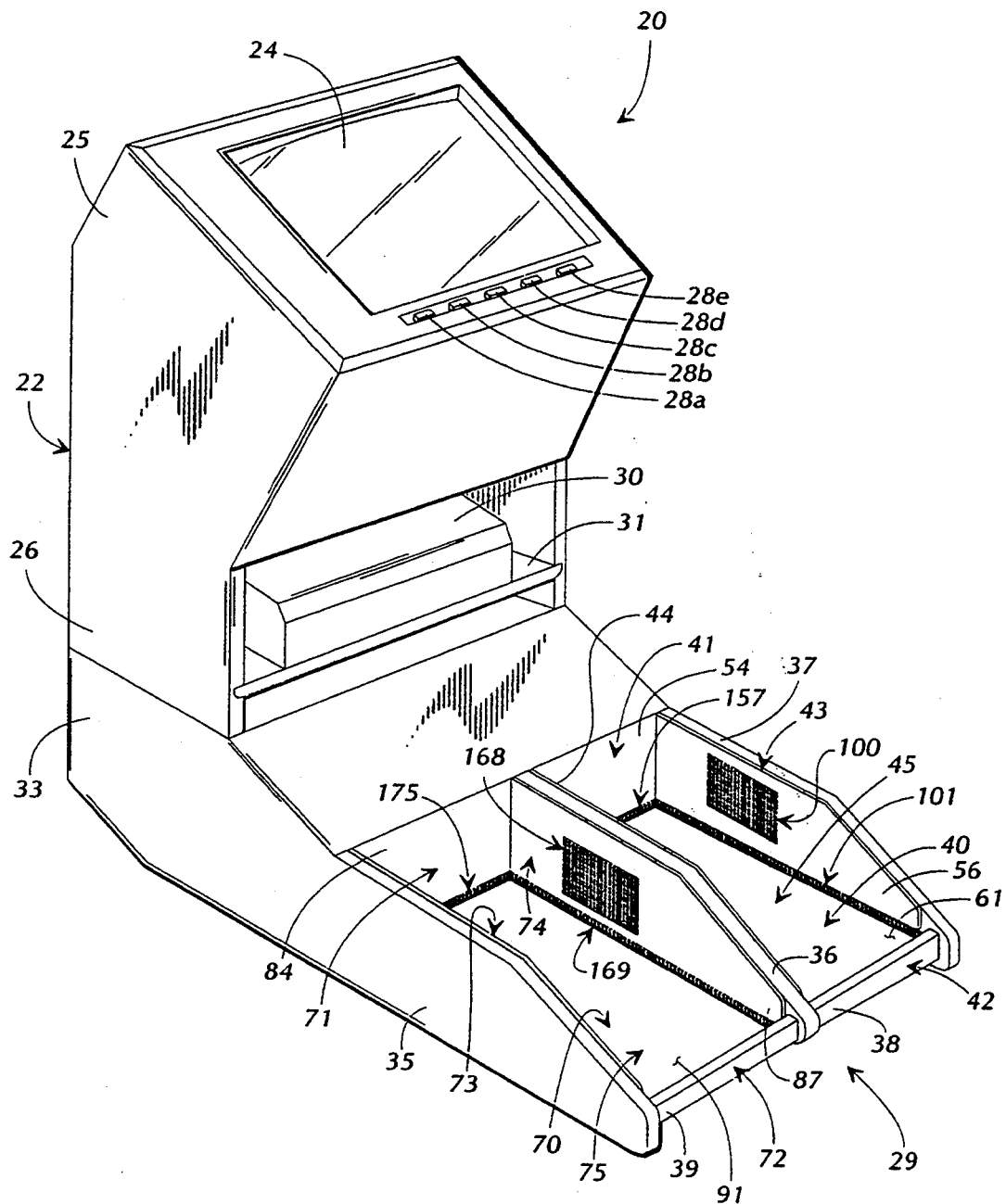
FIG. 1 is a perspective view of an Apparatus for Analyzing Feet in accordance with the preferred embodiment of the present invention.

Referring now to the drawings, in which like numerals represent like components throughout the several views, a foot measuring system 20, in accordance with the preferred embodiment of the present invention, is shown in FIG. 1. A frame structure 22 is shown including a monitor housing 25 which houses a monitor 24 and supports lighted control buttons 28a–e. The frame structure 22 also includes a controller housing 33 and a printer housing 26 which houses a printer 30 resting on a slidably mounted printer shelf 31. Furthermore, the frame structure 22 includes a left panel 35 and a right panel 37 extending outward from the controller housing 33 to border a sensor assembly 29.

A left foot well 70 and a right foot well 40 are shown defined by the sensor assembly 70 between the left and right panels 35, 37. The floor of the left foot well 70 is represented as a left pressure pad assembly 75 including a left pad cover 91, and the floor of the right foot well 40 is represented as a right pressure pad assembly 45 including a right pad cover 61. Four infrared (IR) assemblies circumscribe each foot well 40, 70. Namely, a left front IR assembly 71, a left rear IR assembly 72, a left outer IR assembly 73, and a left inner IR assembly 74 circumscribe the left foot well 70; a right front right front IR assembly 41, a right rear IR assembly 42, a right outer IR assembly 43, and a right inner IR assembly 44 circumscribe the right foot well 40.

The left inner IR assembly 74 includes a left height transmitter array 168 and a left length transmitter array 169 mounted upon a left inner IR board 81 (substantially hidden from view), and the right outer IR assembly 43 includes a right height transmitter array 100 and a right length transmitter array 101 mounted upon a right outer IR board 50 (substantially hidden from view). Although hidden from view in FIG. 1, the left outer IR assembly 73 includes a correspondingly positioned left height receiver array 171 and a left length receiver array 172 mounted upon a left outer IR board 80, and the right inner IR assembly 44 includes a correspondingly placed right height receiver array 135 and a right length receiver array 136 mounted upon a right inner IR board 51. The left front IR assembly includes a left width receiver array 175 mounted upon a left front IR board 78 (substantially hidden from view), and the right front IR assembly 41 includes a right width receiver array 157 mounted upon a right front IR board 48 (substantially hidden from view). Likewise, although hidden from view in FIG. 1, the left rear IR assembly 72 includes a correspondingly placed left width transmitter array 180 mounted upon a left rear IR board 79, and the right rear IR assembly 42 includes a correspondingly placed right width transmitter array 125 mounted upon a right rear IR board 49.

A center panel 36 is shown extending between the left inner IR assembly 74 and the right inner IR assembly 44. The left inner IR assembly 74 further includes a left inner cover 87 which substantially obscures the underlying left inner IR board 81 and ends immediately above the left length transmitter array 169. The left inner cover 87 is generally opaque except for a clear portion positioned over the left height transmitter array 168. A right outer cover 56 included in the right outer IR assembly 43 is very similar to the left inner cover 87, and corresponding covers are included in the left outer IR assembly 73 and the right inner IR assembly 44. The left front IR assembly 71 and the right front IR assembly 41 include a left front cover 84 and a right front cover 54, respectively, which are completely opaque and extend downward to locations immediately above the left width receiver array 175 and the right front receiver array 157. The left rear IR assembly 72 and the right rear IR assembly 42 are shown including a left kick guard 39 and a right kick guard 38, respectively.

FIG. 2 shows a left side view of the foot measuring system 20. The monitor 24 is shown extending downward into the monitor housing 25 of the frame structure 22, and the printer 30 is shown resting on the printer shelf 31 mounted inside the printer housing 26. A controller 200 is shown mounted inside a controller drawer 34 which is slidably mounted inside the controller housing 33. One frame wheel 23a of two 23a,b is shown mounted to the underside of the controller housing 33 of the frame structure 22.

Figure 10A:
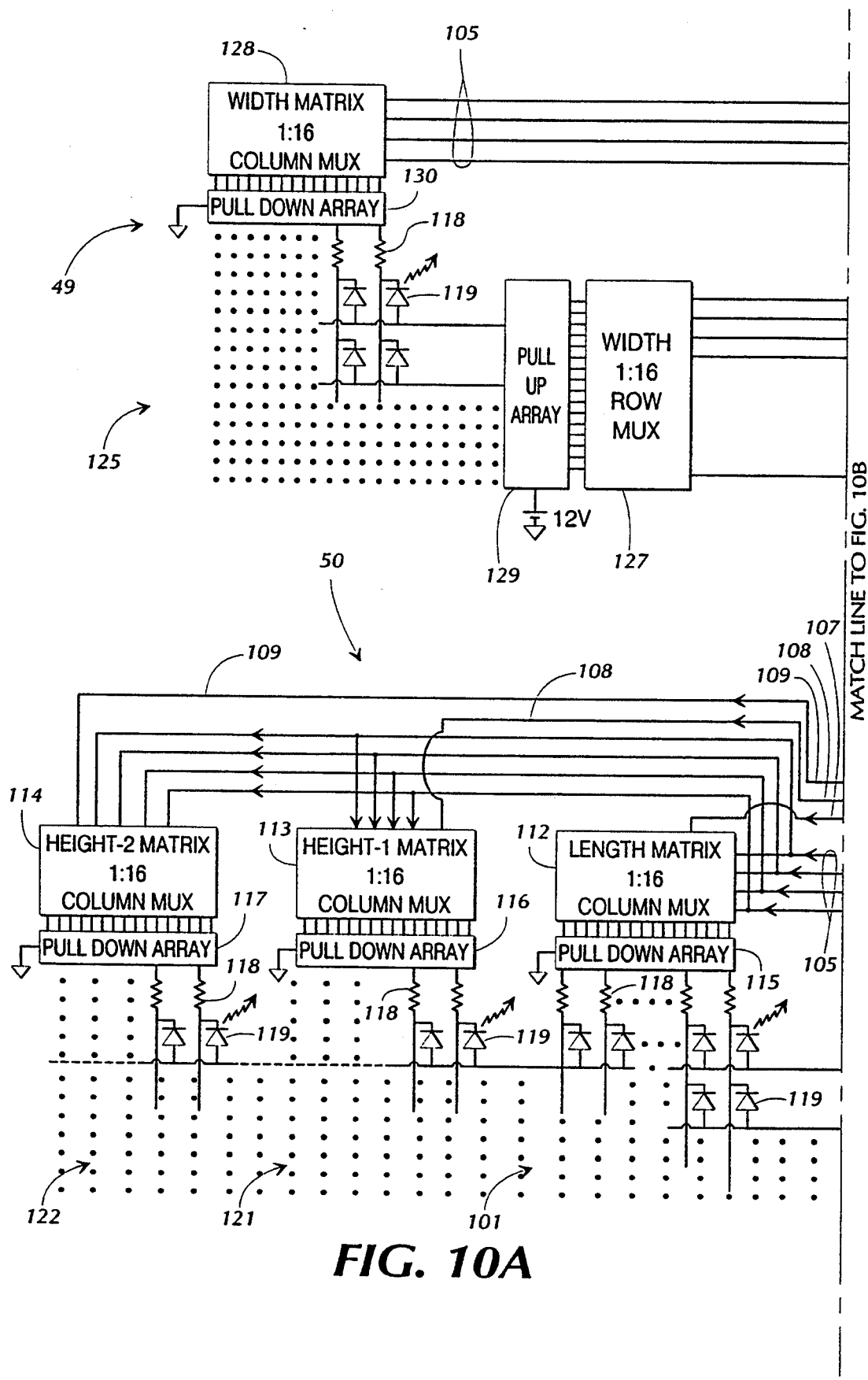
FIG. 10 is a block diagram representation of the right outer IR board and the right rear IR board of FIG. 6.
Figure 10B:
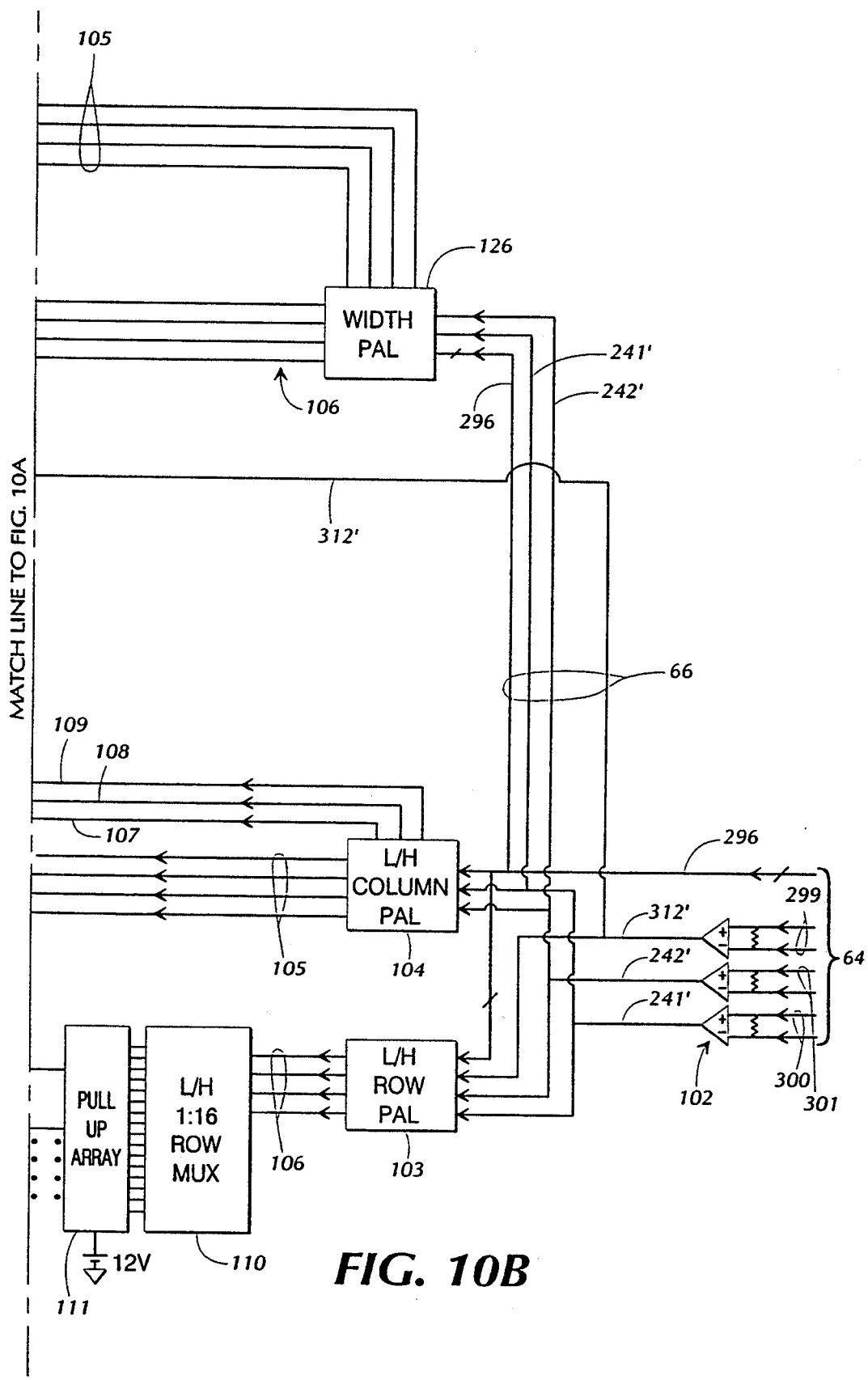

A more detailed view of the area designated as area "A" is shown in FIG. 2(a) which shows a cross-sectional view of the left panel 35, the left rear IR assembly 72, and the left pressure pad assembly 75. The left rear IR assembly 72 is shown including the left kick guard 39 and the left rear IR board 79, complete with the left width transmitter array 180. The left pressure pad assembly 75 is shown including a left pad contact board 90 and a left pad cover 91 which rest upon a mounting plate 21 which extends below the entire sensor assembly 29 and is supported by the kick guards 39, 38 (FIG. 1) and the left and right panels 35, 37 (FIG. 10). The left inner IR assembly 74 is also shown including the left inner cover 87 and the left inner IR board 81 interposed between the left inner cover 87 and the center panel 36 and upon which the left length transmitter array 169 is mounted.

A more detailed view of the area designated as area "B" is shown in FIG. 2(b) which shows a section immediately inside the left panel 35, behind the left outer IR board 80, and adjacent the controller housing 33. The mounting plate 21 is shown supporting the left pad contact board 90 and the left pad cover 91, and the left front IR assembly 71 is shown including a left gain boosting lamp 179 and the left width receiver array 175 mounted upon the left front IR board 78 which is behind the left front cover 84. A left sensor connector 261 is shown connecting the left pad contact board 90 to a mux board 260 which, as is discussed in greater detail below, is connected to a processor adapter 220 which connected to the controller 200 mounted inside the controller drawer 34.

Figure 5:
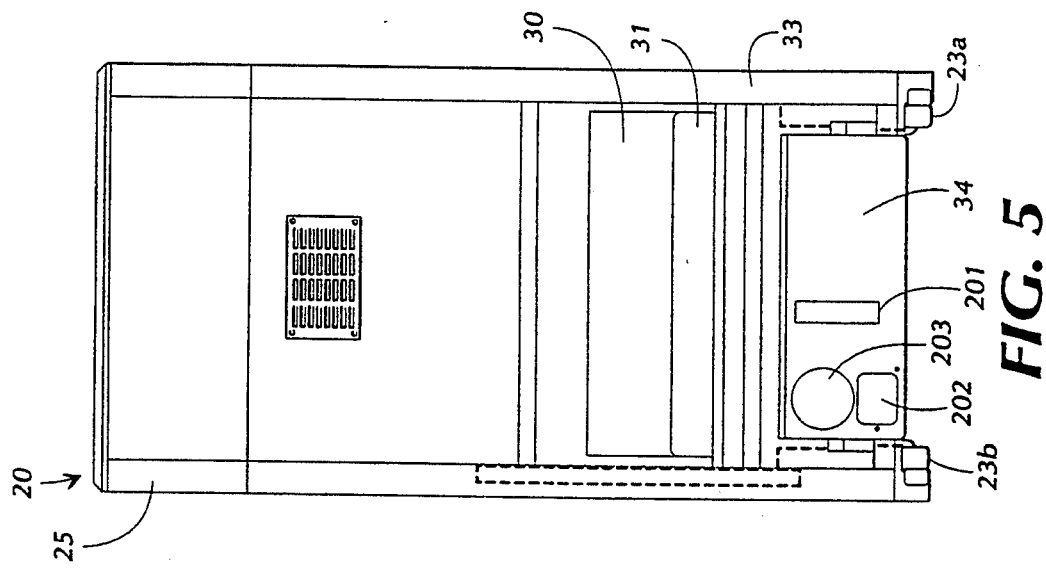
FIG. 5 is a rear view of the apparatus of FIG. 1.
Figure 4:
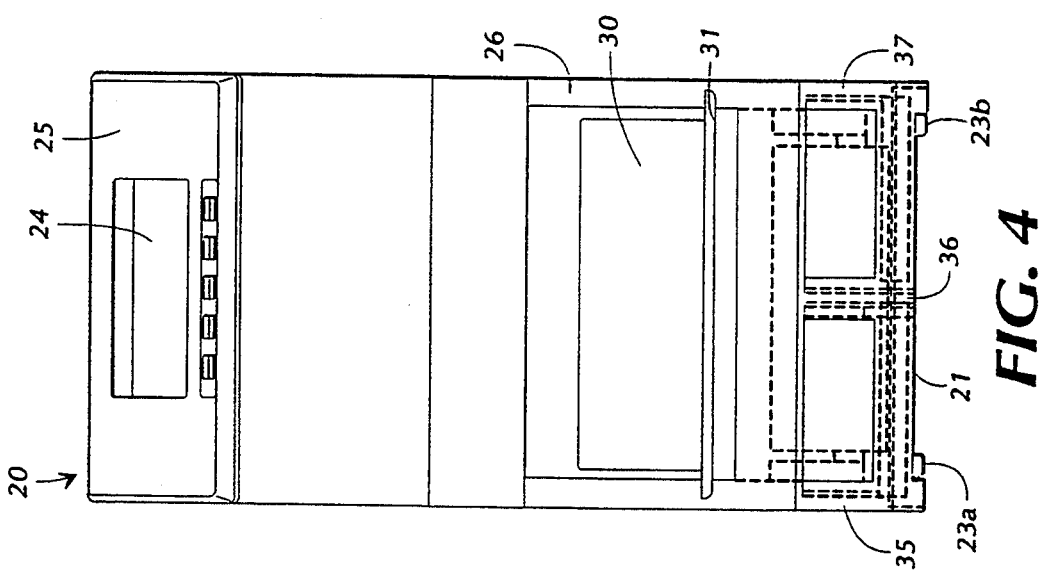
FIG. 4 is a front view of the apparatus of FIG. 1.
Figure 3:
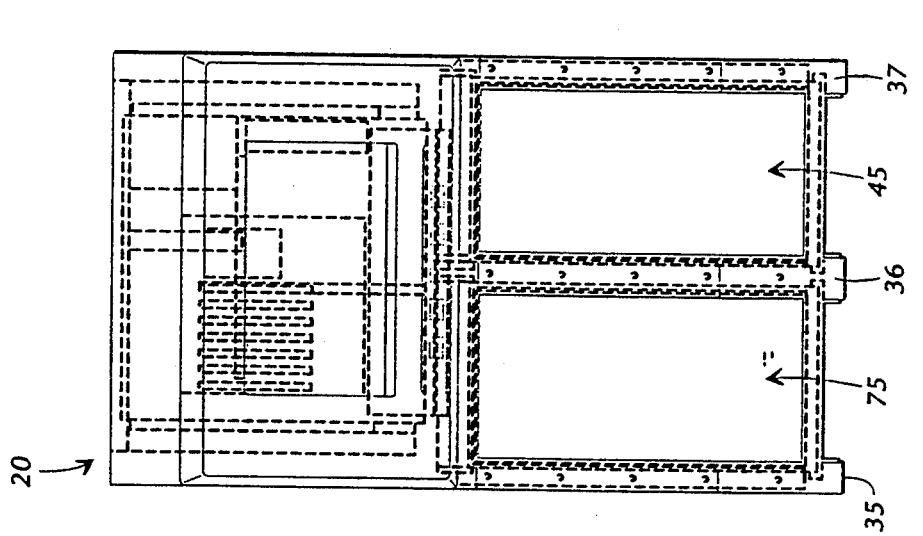
FIG. 3 is a top view of the apparatus of FIG. 1.

FIGS. 3-5 show top, front, and rear views, respectively, of the foot measuring system 20. Both frame wheels 23a,b are shown in FIGS. 4 and 5. Also, a floppy drive 201, power supply 202, and fan 203 are shown extending through the controller drawer 34.

Figure 6:
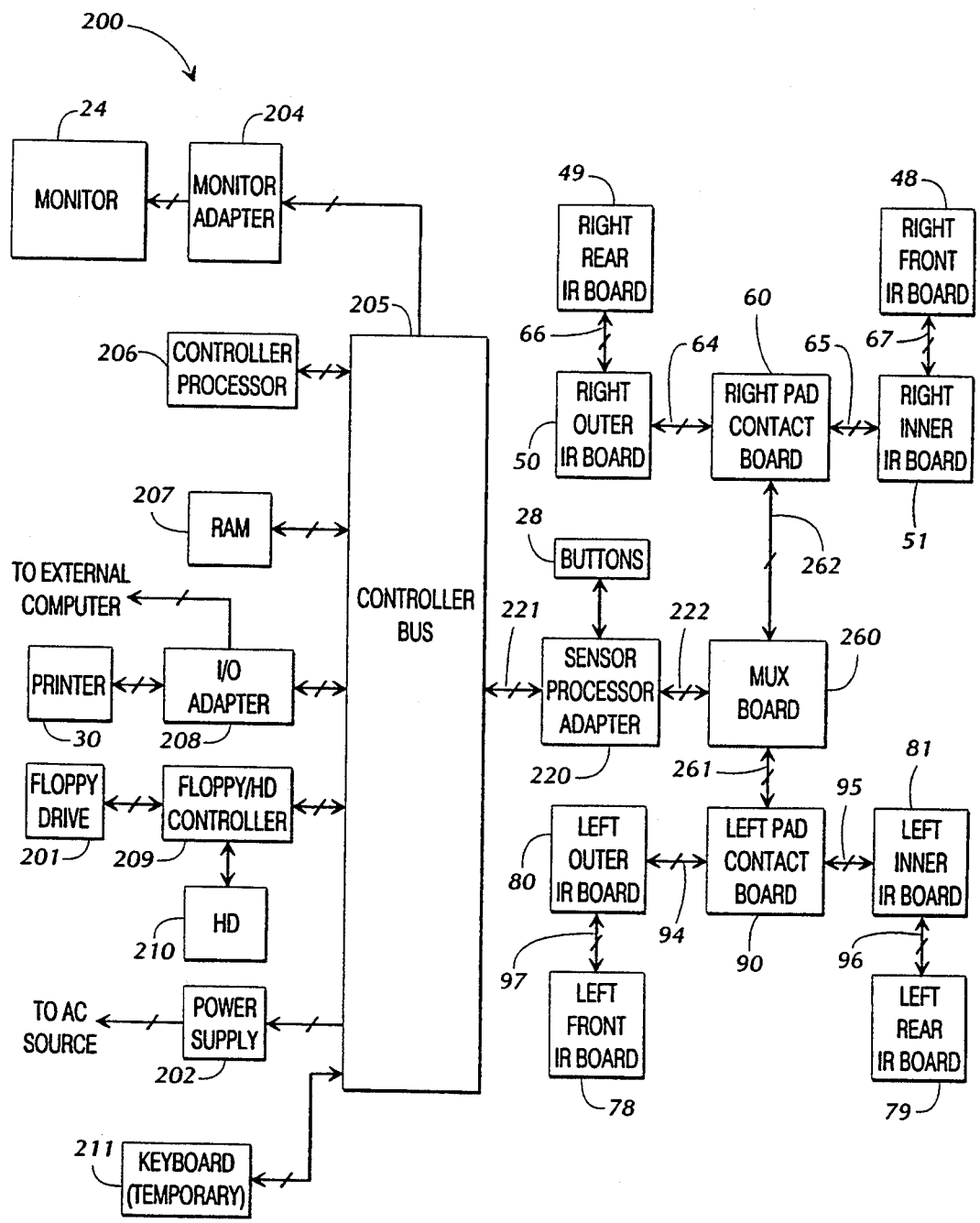
FIG. 6 is a block diagram representation of the electronic components of the apparatus for analyzing feet in accordance with the preferred embodiment of the present invention.

FIG. 6 shows a block diagram representation of the electronic components of the foot measuring system 20 in accordance with the preferred embodiment of the present invention. The controller 200 is shown connected to the monitor 24 through a monitor adapter 204 which is connected to a controller bus 205. A controller processor 206 and random access memory (RAM) are also show connected to the controller bus 205. The printer 30 is shown connected to the controller bus 205 through an input/output (I/O) adapter 208 which also provides a link to any external computers or devices. The floppy drive 201 is shown connected to the controller bus 205 through a floppy/hard drive controller 209 which is also connected to a hard drive 210. The power supply 202 connects the controller 200 to an AC source, and a user may temporarily attach a keyboard for maintenance, testing, etc. One example of an acceptable controller 200 is an industry standard personal computer (PC) with an industry standard IBM ® PC AT ® bus.

The controller bus 205 is also connected through a sensor process-controller connector 221 to the sensor processor adapter 220, which is discussed in greater detail below. The buttons 28 are shown connected to the sensor processor adapter 220. The mux board 260, also discussed in greater below, is connected to the sensor processor adapter through a sensor processor-mux connector 222.

A right pad contact board 60 is connected to the mux board 260 through a right sensor connector 262, to the right outer IR board 50 through a right outer connector 64, and to the right inner IR board 51 through a right inner connector 65. The right rear IR board 49 is connected through a right rear connector 66 to the right outer IR board 50, and the right front IR board 48 is connected through a right front connector 67 to the right inner IR board 51. The left pad contact board 90 is connected to the mux board 260 through the left sensor connector 261, to the left outer IR board 80 through a left outer connector 94, and to the left inner IR board 58 through a left inner connector 95. The left rear IR board 79 is connected through a left rear connector 96 to the left inner IR board 81, and the left front IR board 78 is connected through a left front connector 97 to the left outer IR board 80. Each of the right boards 48-51, 60 are discussed in greater detail below. According to the preferred embodiment of the present invention, the left boards 78-81, 90 are essentially identical to the corresponding right boards 48-51, 60, being interchangeable therewith, and are not discussed further.

Figure 7A:
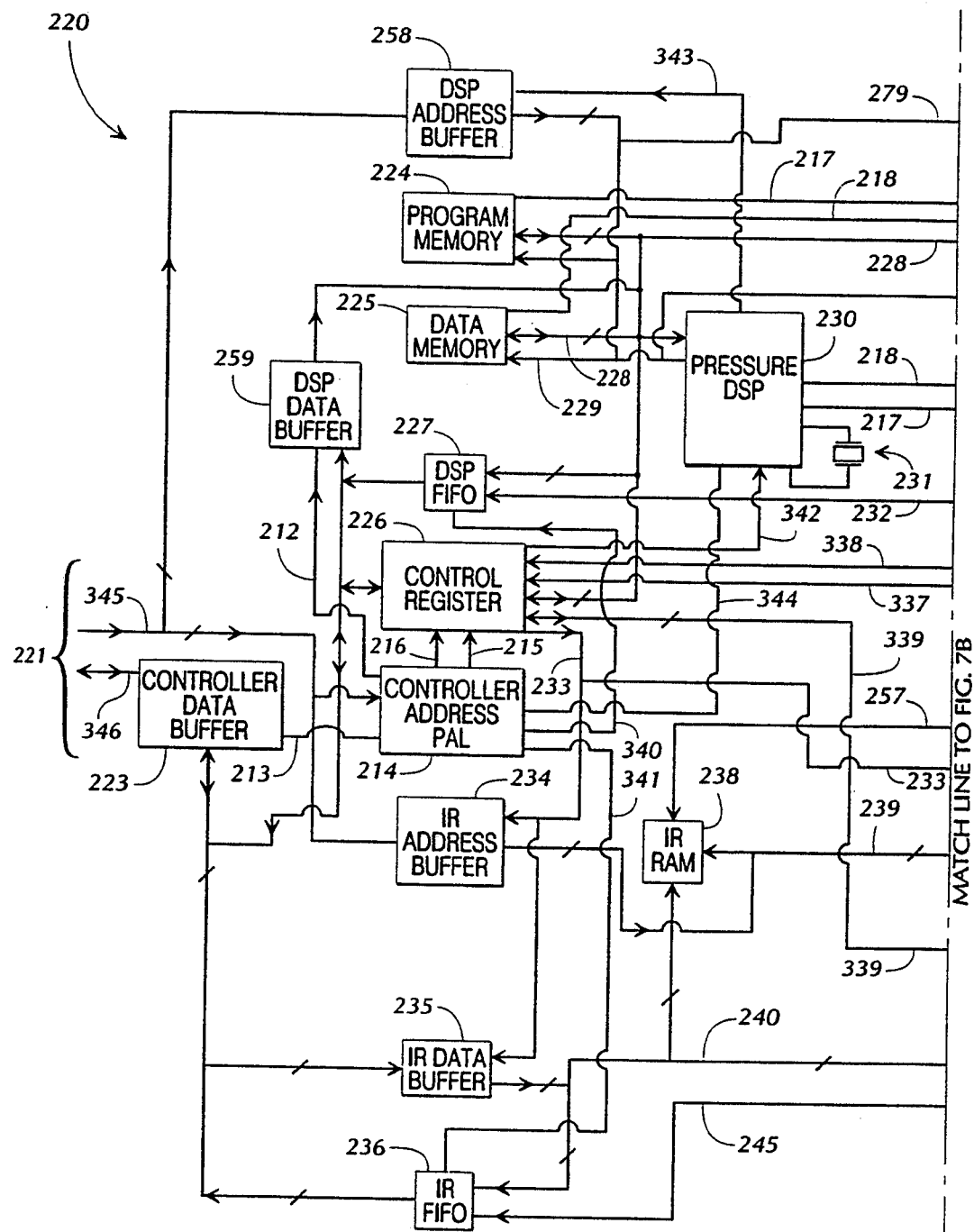
FIG. 7 is a block diagram representation of the sensor processor adapter and buttons of FIG. 6.
Figure 7B:
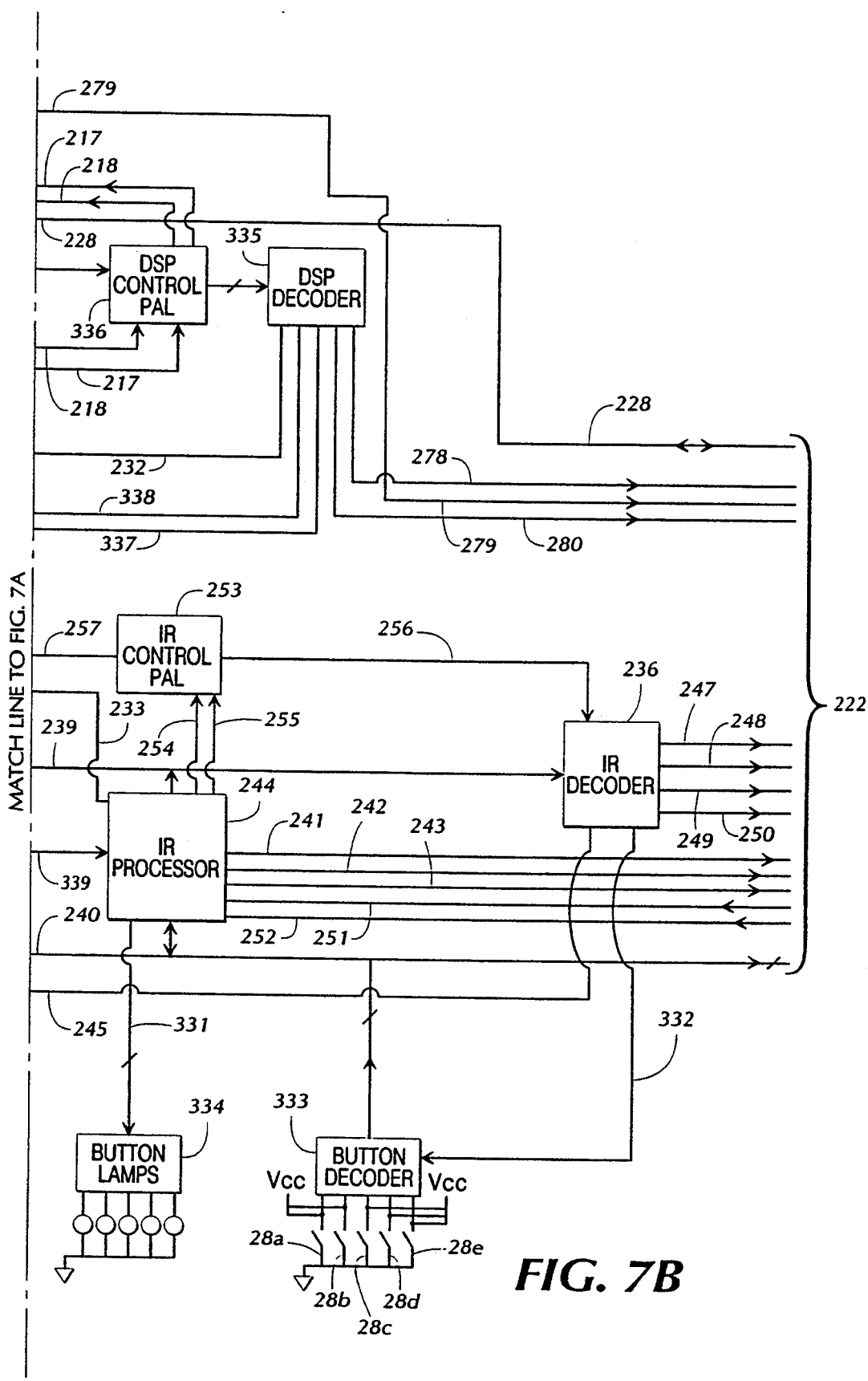

Refer now to FIG. 7, which shows a block diagram representation of the sensor processor adapter 220. The two central components of the sensor process adapter 220 are a digital signal processor (DSP) for the pressure system, denoted pressure DSP 230, and a microprocessor for the optical system, denoted IR processor 244. An example of an acceptable pressure DSP 230 is the ADSP-2105KP-40 from Analog Devices of Norwood, Mass. An example of an acceptable IR processor 244 is the MC68HC11F1FN from Motorola of Phoenix, Ariz.

In alternate embodiments, the pressure DSP 230 and IR processor 244 are combined into a single processor.

The sensor processor-controller connector 221 is shown including, at least, a controller address bus 345 and a controller data bus 346. The controller address bus 345 is shown connected to a controller address programmable array logic (PAL) 214, an infrared (IR) address buffer 234, and a pressure address buffer 258. The controller data bus 346 is shown connected to a controller data buffer 223, through which the data bus 346 is connected to an IR first-in-first-out (FIFO) memory 236, an IR data buffer 235, a control register 226, a DSP FIFO 227, and a DSP data buffer 259.

The DSP address buffer 258 is connected to a DSP address bus 229 and gates the controller address buffer 345 onto the DSP address bus 229 upon receiving a control signal from the pressure DSP 230 along a bus grant line 343. One or more bits of the DSP address bus 229 are also connected to a program memory 224, a data memory 225, a DSP control PAL 336, and the sensor processor-mux connector 222 as read/convert selector 279. The DSP control PAL 336 is connected to the data memory 225 and program memory 224 through data memory select line 218 and program memory select 217, respectively, which originate with the pressure DSP 230. One or more bits of the DSP data bus 228 connect between the DSP data buffer 259, the program memory 224, the data memory 225, the DSP FIFO 227, the control register 226, the pressure DSP 230, and the sensor processor-mux connector 222. A DSP clock 231 is shown connected to the pressure DSP 230. The DSP decoder 335 is shown connected to the DSP FIFO through a FIFO written line 232, and to the control register 226 through read handshaking bit line 337 and write handshaking bit 338. The DSP controller 335 also connects to a row/column enable 278 and to an A-to-D enable 280 which exit the sensor processor adapter 220 through the sensor processor-mux connector 222.

The control register 226 represents a plurality of latches and buffers designed to interact with the controller address PAL 226 and other elements to control operation of the sensor processor adapter 220. The controller address PAL 214 is also connected to the DSP data buffer through DSP data buffer enable 212, to controller data buffer 223 through controller data buffer enable 213, to DSP FIFO 227 through DSP FIFO read enable 340, to the pressure DSP 230 through a DSP reset 344, and to the IR FIFO 236 through an IR FIFO read enable 341. The control register 226 sends signals along a DSP bus request 342 to the pressure DSP 230. The control register 226 is also connected through IR handshaking controls 339 to IR processor 244, and through IR address buffer select/IR process reset 233 to IR address buffer 234, IR data buffer 235, and IR processor 244.

One or more bits of an IR address bus 239 run between the IR address buffer 234, an IR RAM 238, the IR processor 244, and an IR decoder 236. Also, one or more bits of an IR data bus 240 run between the IR FIFO 236, the IR data buffer 235, the IR RAM 238, the IR processor 244, the button decoder 333, and the sensor processor-mux connector 222. A chip select program line 254 and a chip select general purpose line 255 connect the IR processor 244 to an IR control PAL 253 which, by virtue of the RAM chip select line 257, maps all writes from the IR data bus 240 into the IR RAM 238 and enables the IR decoder 236 for certain addresses on the IR address bus 239. Based on the address on IR address bus 240, the IR decoder 236 generates signals on the right receiver control 247, right transmit control 248, left receiver control 249, left transmit control 250 (all exiting the sensor processor adapter 220 through the sensor processor-mux connector 222), button decode enable 332 connected to the button decoder 333, or a write FIFO line 245 connected to the IR FIFO 236.

The IR processor 244 also generates signals to the button lamp control 334 through button lamp control lines 331. Also, the IR process 244 generates a serial peripheral interface (SPI) data signal 241, a right SPI clock 242, and a left SPI clock 243 which exit the sensor processor adapter 220 through the sensor processor-mux connector 222. Two signals, a right IR_seen 251 and a left IR_seen 252 are shown entering the IR processor from the sensor processor-mux connector 222.

Figure 8A:
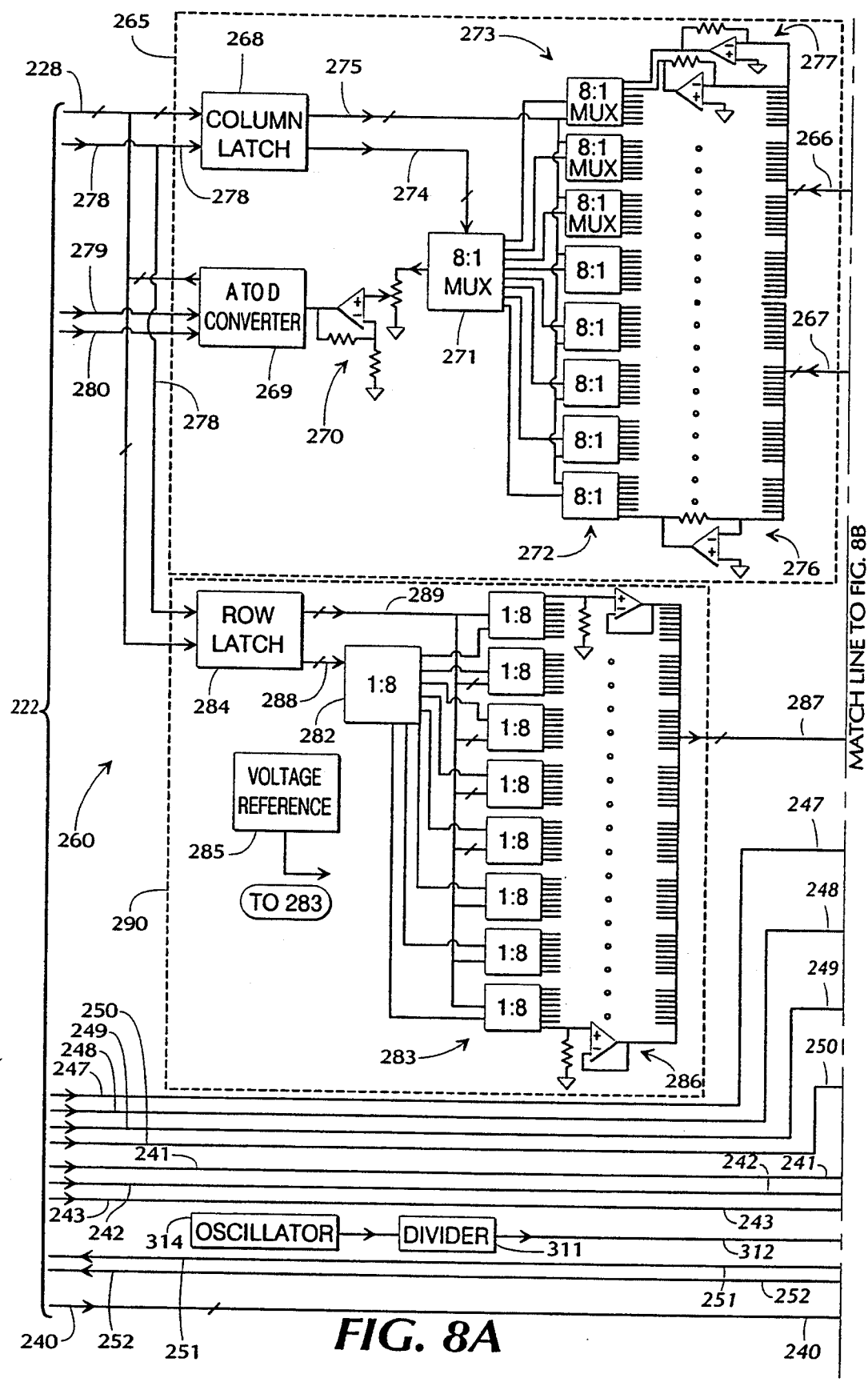
FIG. 8 is a block diagram representation of the mux board of FIG. 6.
Figure 8B:
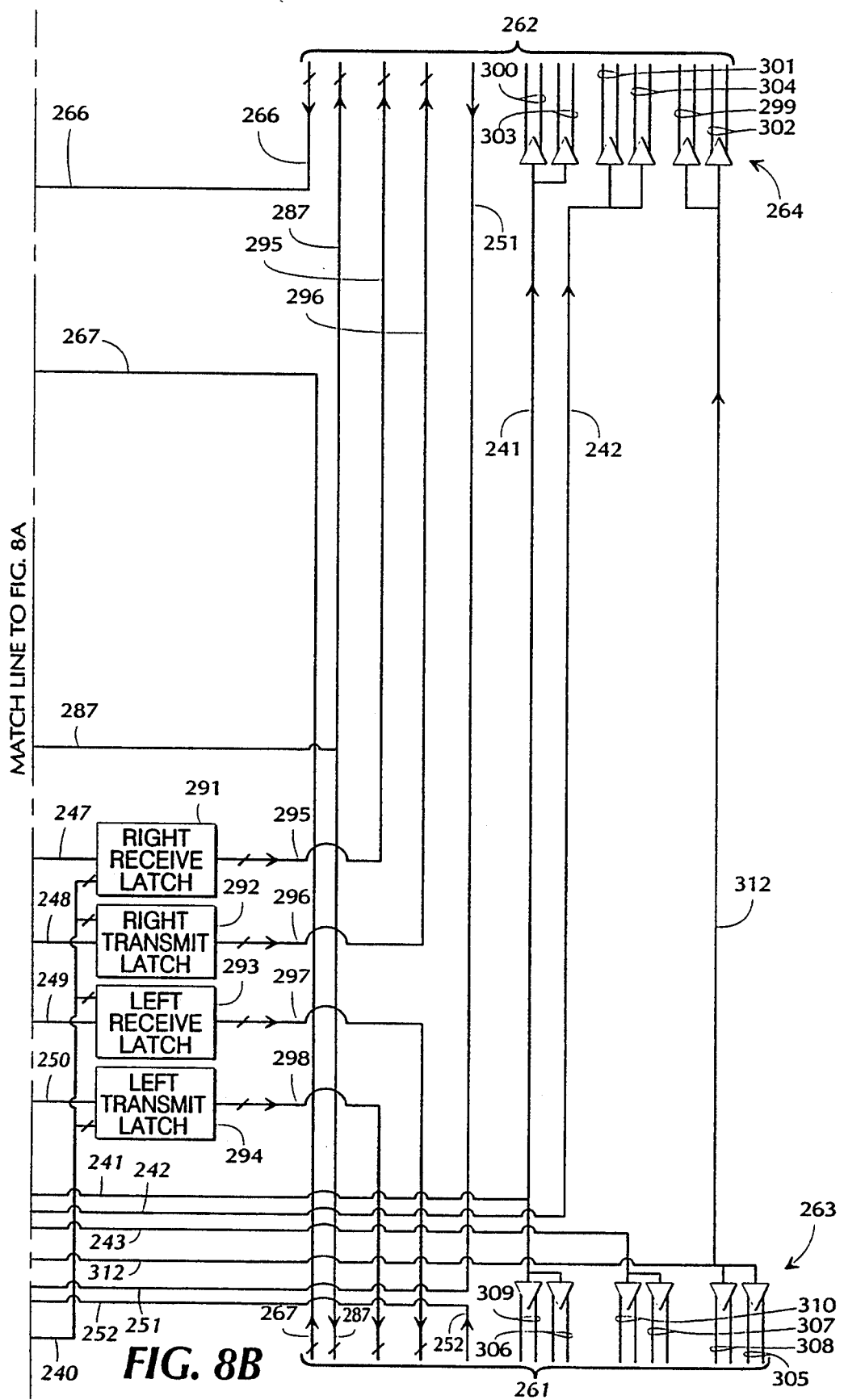

Refer now to FIG. 8, which shows a block diagram of the mux board 260 in accordance with the preferred embodiment of the present invention. The sensor processor-mux connector 222 is shown including the identical lines leaving the sensor processor adapter 220. The DSP data bus 228, row/column enable 278, read/convert selector 279, and A-to-D enable 280 are shown connected to a column driver 265, and the DSP data bus 228 and row/column enable 278 are shown connected to a row driver 290. The column driver 265 includes a column latch 268 which receives input from the DSP data bus 228 and the row/column enable 278. An upper column mux select 274 connects the column latch 268 to an 8:1 analog multiplexer 271, and a lower column mux select 275 connects the column latch 268 to a lower column 8:1 analog mux bank 272, each of which are also connected to the 8:1 analog multiplexer 271. A left current to voltage (I-to-V) converter bank 276 of, in the preferred embodiment, 32 converters, supplies input from left column select lines 267 which exit the mux board 260 through the left sensor connector 261, and a right I-to-V convert bank 277 of, in the preferred embodiment, 32 converters, supplies input from right column select lines 266 which exit the mux board 260 through the right sensor connector 261. Output from the 8:1 analog mux 271 flows through a gain adjuster 270 and into the A-to-D converter 269 which supplies output onto the DSP data bus 228 according to control signals received through the read/convert selector and A-to-D enable 280.

The row driver 290 includes a row latch 284 receiving input from the DSP data bus 228 and the row column selector 278. An upper row mux select 288 connects the row latch 284 to an upper 1:8 mux 282, and a lower row mux select 289 connects the row latch 284 to a lower 1:8 analog mux bank 283, which also receive input from the upper 1:8 mux 282 and a voltage reference source 285 which, in the preferred embodiment, supplies −1.0 volts. The output from the lower 1:8 analog mux bank 283 is connected to a voltage source bank 286 of, in the preferred embodiment, 64 sources which are connected to row select lines 287 which exit the mux board through both the left and right sensor connectors 261, 262.

The right receive control 247, right transmit control 248, left receive control 249, and left transmit control 250 are shown connected to a right receive latch 291, a right transmit latch 292, a left receive latch 293, and a left transmit latch 294, respectively. One of these control lines 247–250 will cause one of these latches 291–294 to latch data from the IR data bus 240, which is also connected to each of the latches 291-294. Output from the latches 291-294 exit the mux board 260 along right receive matrix select 295, right transmit matrix select 296, left receive matrix select 297, and left transmit matrix select 298, respectively. An oscillator 314 is shown connected to a divider 311 with output along modulator line 312. The SPI data line 241, right SPI clock line 242, and left SPI clock line 243, along with the modulator line 312, are shown connected to a left differential driver bank 263 and/or a right differential driver bank 264 to convert the TTL signals into differential signals right transmit SPI data lines 300, right receive SPI data lines 303, right transmit SPI clock lines 301, right receive SPI clock lines 304, right transmit modulator lines 299, right receive modulator lines 302, left transmit SPI data lines 309, left receive SPI data lines 306, left transmit SPI clock lines 310, left receive SPI clock lines 307, left transmit modulator lines 308, and left receive modulator lines 305. The right and left IR—seen lines 251 and 252 are also shown passing through from the sensor connectors 262, 261 to the sensor processor-mux connector 222.

Figure 9A:
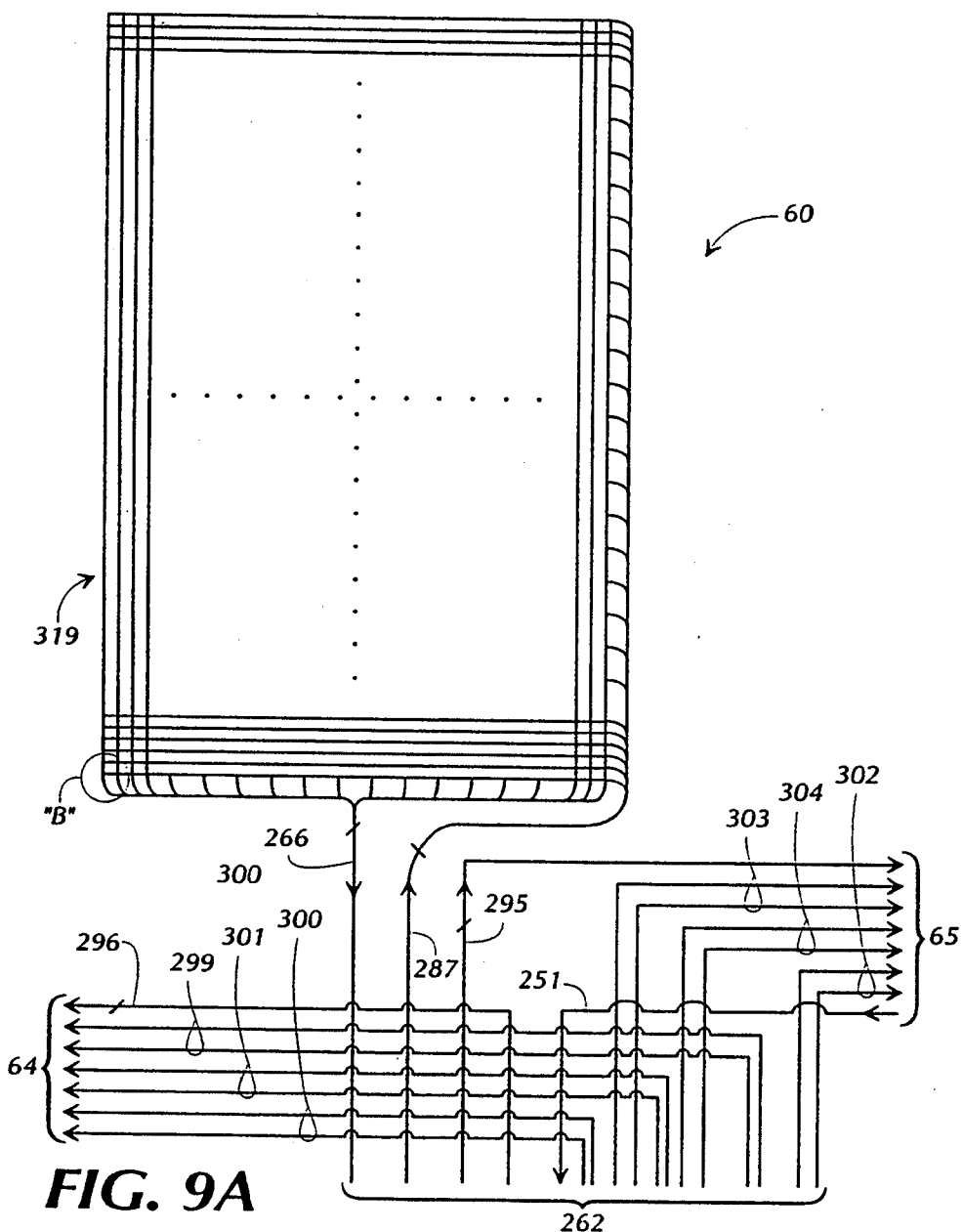
FIG. 9(a) is a block diagram representation of the right pad contact board of FIG. 6.
Figure 9B:
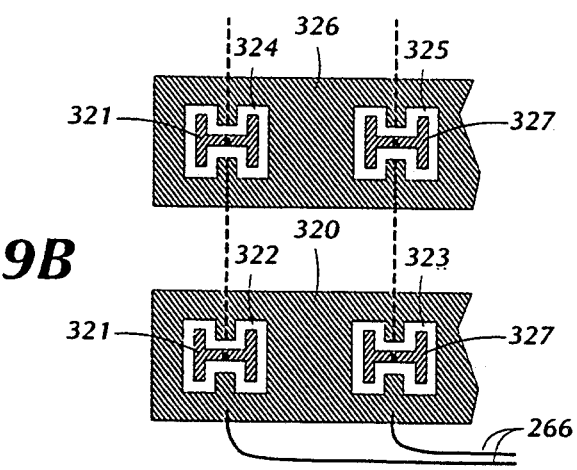
FIG. 9(b) is a detailed view of the are a "B" of FIG. 9(a).

FIG. 9(a) shows a block diagram representation of the right pad contact board 60. The IR signals are shown passing through from the right sensor connector 262 to either the right outer connector 64 or right inner connector 65. The row select lines 287 are shown supplying current to the rows of a right contact array 319, and the right column select lines 266 are shown receiving current from the columns of the right contact array 319. The area designated as area "B" is shown in more detail in FIG. 9(b) to include a row 1 connector 320 and a row 2 connector 326 which define insulator gaps referred to as R1C1 insulator gap 322, R1C2 insulator gap 323, R2C1 insulator gap 324, and R2C2 insulator gap 325. Column 1 conductor 321 and column 2 conductor 327 are shown connected to the right column select lines 266 and protruding into the insulator gaps without touching the row conductors 320, 326. The right pad cover 61 (FIG. 1) bridges the insulator gaps to act as a matrix of pressure sensitive, variable resistors.

Refer now to FIG. 10, which shows a block diagram representation of the right outer IR board 50 and the right rear IR board 49. The right outer connector 64 includes the right transmitter matrix select 296, right transmit modulator lines 299, right transmit SPI clock lines 301, and right transmit SPI data lines 300. Each of the differential lines are converted back into TTL format through a TTL driver bank 102 to reproduce modulator line 312', right SPI clock line 242', and SPI data line 241'. Each of the reproduced lines, along with the right transmit matrix select 296 also proceed through the right rear connector 66 to the right rear IR board 49.

The right transmit matrix select 296 is connected along with the right SPI clock line 242' and SPI data line 241' to a length/height (L/H) column PAL 104, an L/H row PAL 103, and a width PAL 126. The modulator line 312' is connected to the L/H row PAL 103 and a width 1:16 row mux which is connected to the width PAL 126. The L/H column PAL 104 shifts the serial data coming from the SPI data line 241' into parallel format and sends the upper nibble through SPI upper nibble lines 105 to a length matrix column mux 112, a heigth-1 matrix column mux 113, and a heigth-2 matrix column mux 114 and enables each through length matrix select 107, height-1 matrix select 108, and height-2 matrix select 109 based upon data received through the right transmit matrix select 296. Similarly, the width PAL shifts the upper nibble of the SPI data to a width matrix column mux 128. The column mux's 112-114, 128 are shown connected to pulldown arrays 115-117, 130, which effectively pull selected columns down to ground through column resistors 118 upon selection. Examples of acceptable pull down arrays are ULN-2803 from Sprague of Worcester, Mass.

The L/H row PAL 103 also shifts the SPI data, but sends the lower nibble through lower nibble lines 106 to a L/H row mux 110 which is connected to a pull up array 111 which effectively supplies +12 volts to selected rows. Similarly, the width PAL 126 sends the SPI lower nibble to a width row mux 127 which is connected to a pull up array 129 which supplies +12 volts to selected rows. An example of an acceptable pull up array is the ULN 2981A, also from Sprague. The modulator line 312' modulates the row voltages to, in the preferred embodiment, 40 MHz to reduce errors due to outside light sources.

The columns from the pull down arrays 115-117, 130 and the rows from the pull up arrays 111 and 129 connect to transmitter light emitting diodes (LED's) 119 to form right length transmitter array 101, right heigth-1 transmitter array 121, right height-2 transmitter array 122, and right width transmitter array 125. Although electrically arranged in partially-to-completely filled 16×16 formats for efficient control, the arrays are physically arranged as described above with respect to FIG. 1. For example, the right height-1 and height-2 transmitter arrays 121, 122 combine physically to form the right height transmitter array 100 shown in FIG. 1. As current flows through the transmitter LED's 119, modulated, infrared light is emitted.

Figure 11A:
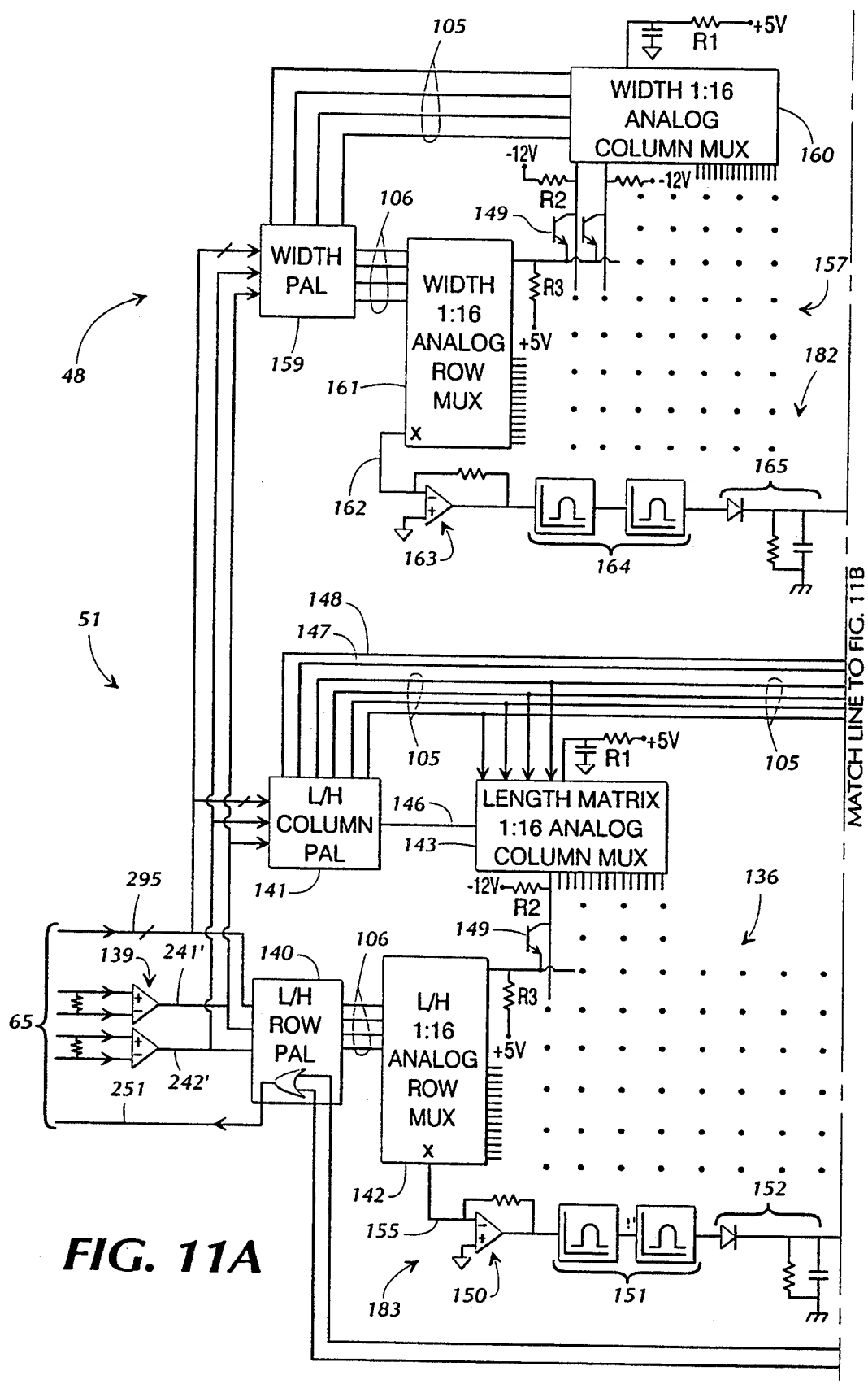
FIG. 11 is a block diagram representation of the right inner IR board and the right front IR board of FIG. 6.
Figure 11B:
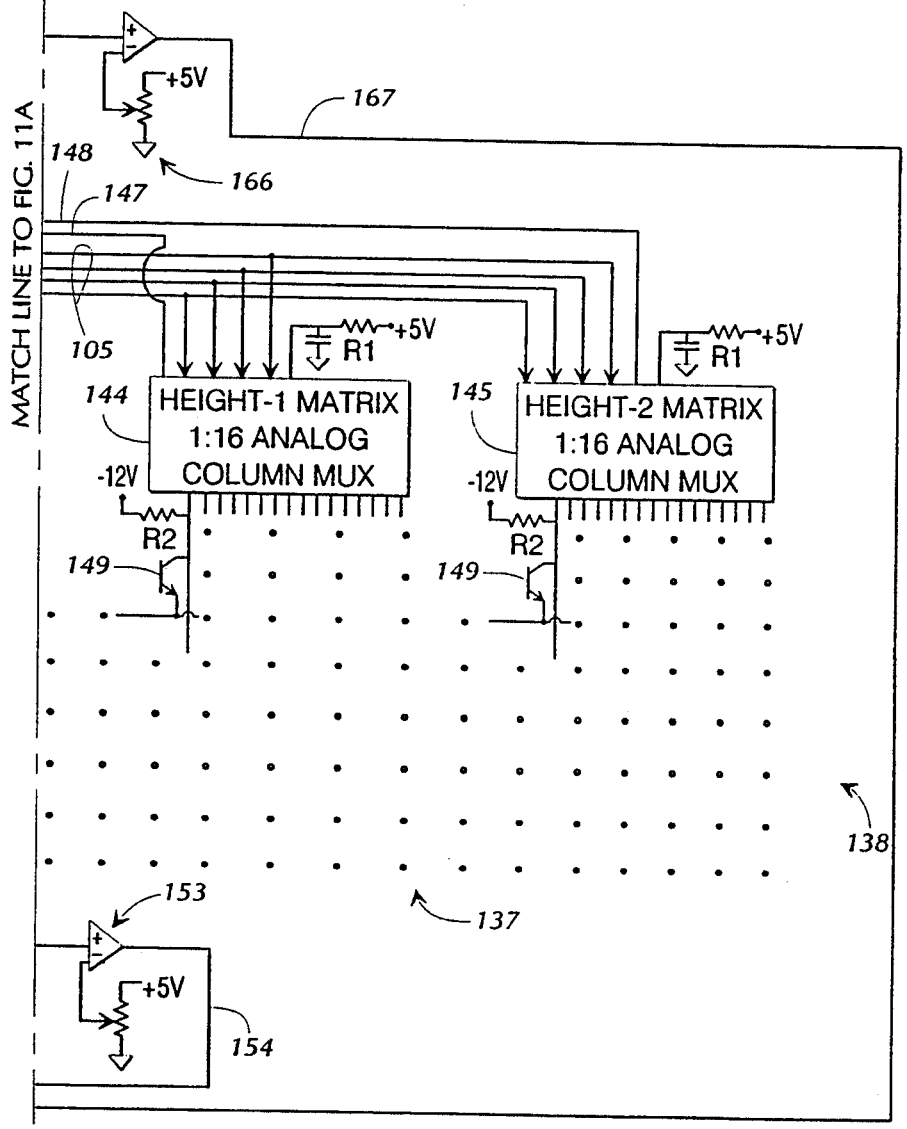

Refer now to FIG. 11, which shows a block diagram representation of the right inner IR board 51 and the right front IR board 48. In a manner very similar to the above discussion, row and column PAL's 140, 141, and 159 are controlled by the right receive matrix select 295 to select a length, width, height-1, or heigth-2 matrix and activate a row and column based on shifted data from the SPI data line 241'. However, pull up and pull down arrays are not utilized, and the multiplexers are analog multiplexers 142-145, 160-161.

As light is received by a selected phototransistor 149 from one of the receiver arrays 136-138, 157, modulated current flows through a row mux 142, 161 and into a modulation filter 182, 183 to detect the modulated signal. Each modulation filter 182, 183 includes an I-to-V converter 163, 150, two band pass filters 164, 151, a peak detector 165, 152, and a comparator 166, 153. A width IR—seen 167 and a L/H IR—seen 154 are connected to a logical "OR" gate within the L/H row PAL 140 to produce the single right IR—seen line 251 which is connected to the right inner connector 65.

Figure 12:
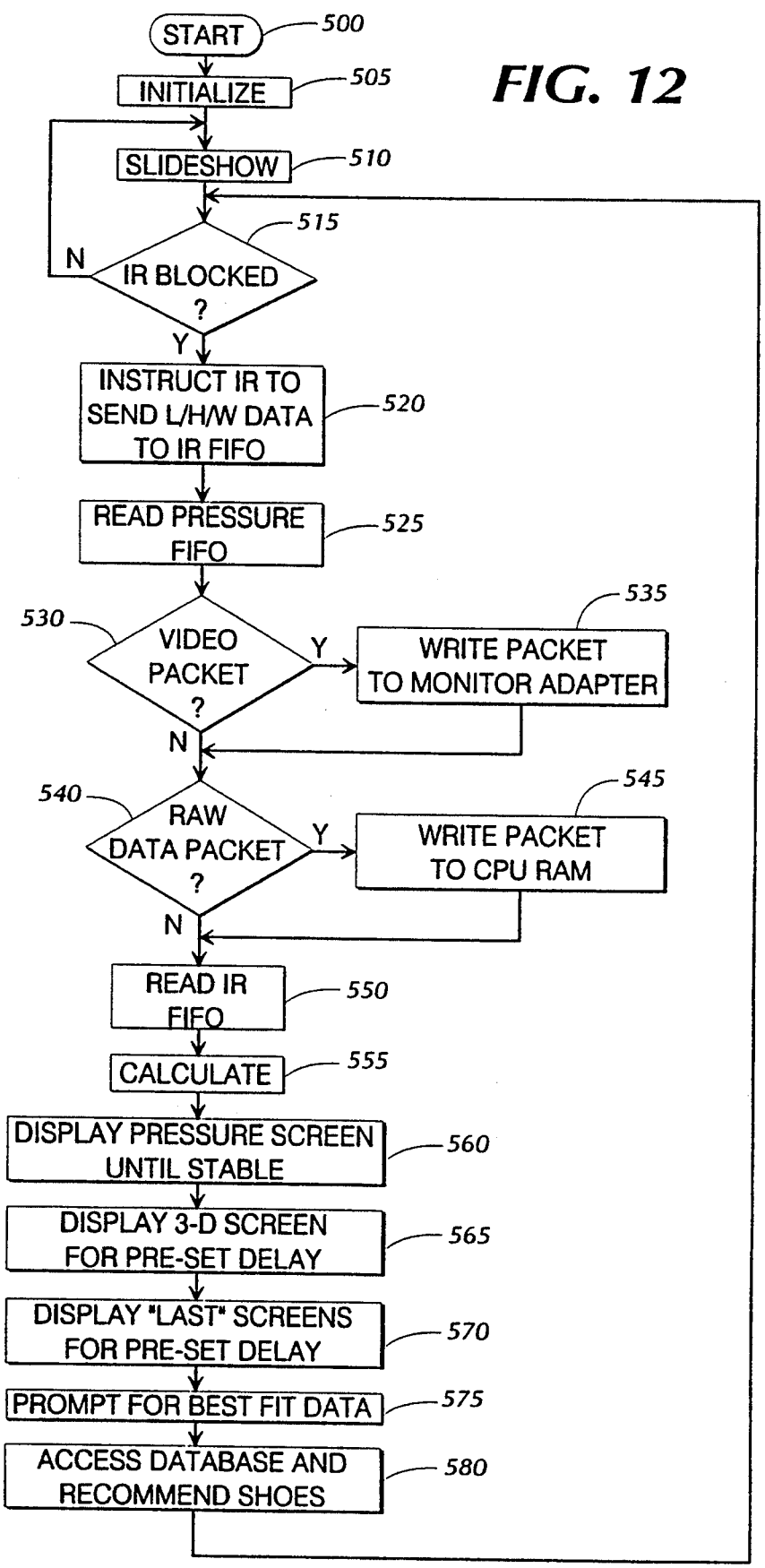
FIG. 12 is a flow chart representation of the steps taken by the controller of FIG. 6.

Refer now to FIG. 12, which shows a flow chart representation of the steps taken by the controller 200 (FIG. 6). For convenience, refer also to FIGS. 6 and 7. After starting at step 500, the controller 200 goes through initialize step 505. Subsequently, an animated slideshow runs in a loop as indicated by decision block 515 until an IR "blocked" packet appears in the IR FIFO 236. The controller programming includes a script means which facilitates modifications to the order and substance of the steps shown in FIG. 12.

After receiving the blocked packet, the controller 200, at step 520, instructs the IR processor 244, through the control register 226, to begin sending length/width- /height packets. At step 525, the controller 200 reads the DSP FIFO 227, which continually attempts to write to the DSP FIFO 227, as is discussed in greater detail below. If the pressure packet obtained is a video packet, decision block 530 sends control to step 535 which indicates that the video packet written directly to the monitor adapter 204, having been formatted by the pressure DSP 230, as is discussed in greater detail below. If the pressure packet is a raw data packet, the decision block 540 and step 545 indicate that the data is written into CPU RAM 207 for analysis. Any available IR packets are then read from the IR FIFO 236 into CPU RAM 207 at step 550 for analysis. Calculations are then made at step 555 with all available data from the pressure and IR systems.

Step 560 indicates that a pressure screen is then displayed until the consumer becomes still and the data becomes stable. Subsequent screens, activated by button 28 or timer, include a 3-dimensional screen in step 565, a "last" screen for each foot at step 570, and best fit data prompting screen at step 575. The buttons 28 are used to control screen advancement, printing, and best fit data selections, and the function of each button 28 may be defined to be screen specific and displayed at the base of each screen. After all the data is verified, the controller 200 accesses a database on the hard drive 210, or through the I/O adapter to an external computer, to match available shoes to a particular consumer. All of the information obtained may also be recorded and matched to a particular consumer for the shoe provider's future reference.

Figure 13:
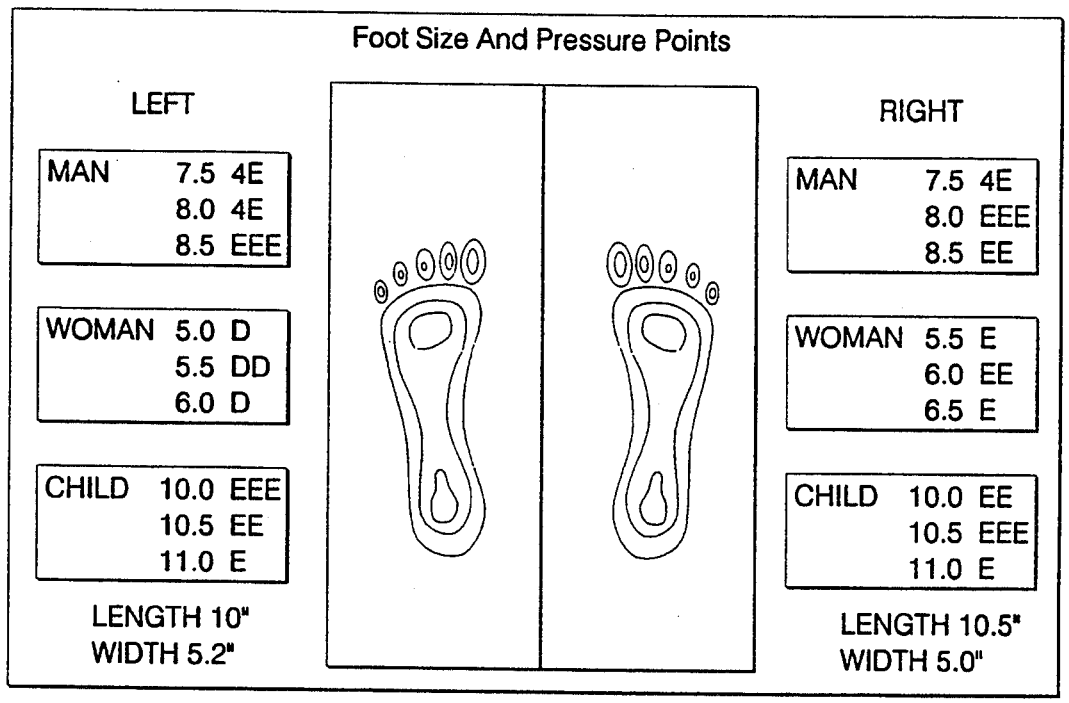
FIG. 13 is a representation of a pressure screen as displayed on the monitor.

One example of an acceptable pressure screen is shown in FIG. 13. All of the data, including the pressure outlines are continually updated while the screen is displayed. Different colors indicated varying amounts of pressure on the pressure outlines. The length and width measurements, derived from the IR packets, for each foot are shown and related to all sizing classes, i.e., man, woman, child, within which ranges the length and width fall. Also, three separate sizes, high medium, and low, for each classification are shown. Adjustments are also made for consumers who stand with feet askew. One method includes comparing the distance from the left-most point to the calculated center of the heel and ball of the foot from the pressure data. If the left-most point is closer to the heel, a ratio is determined based upon the overall width to estimate the actual width. Other methods include calculating angles based on the pressure data to more accurately determine the length and width of an angled foot.

Figure 14:
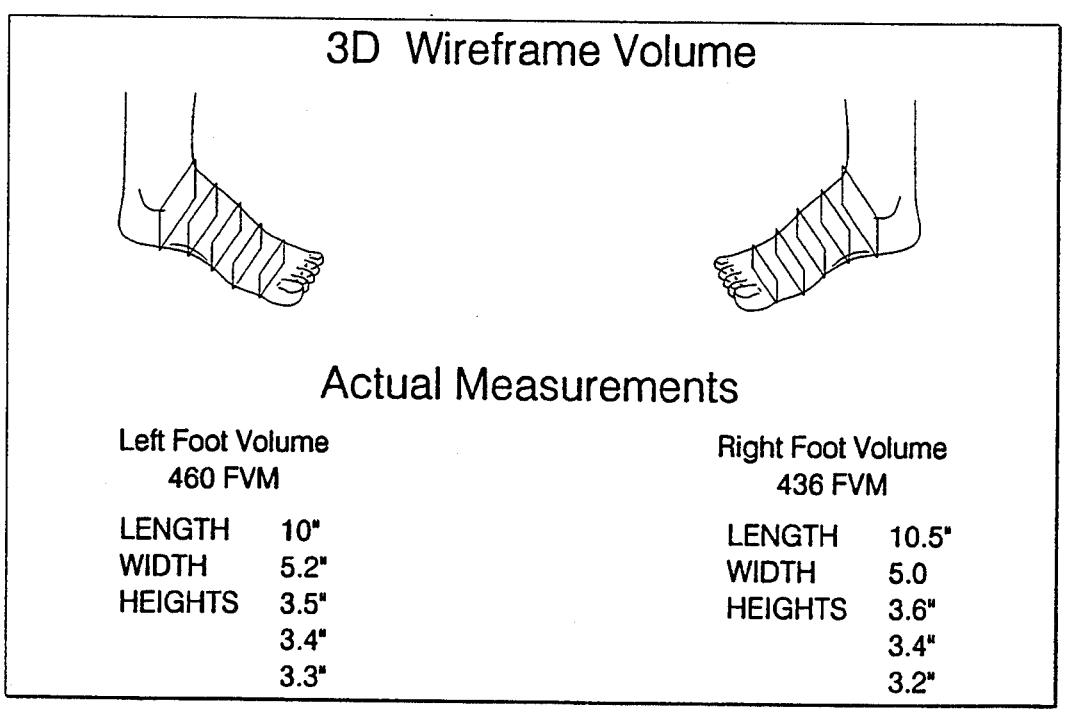
FIG. 14 is a representation of a 3-D wire-frame screen as displayed on the monitor.

FIG. 14 shows an example of an acceptable 3-dimensional screen which sizes a wire-frame model to approximate the size and shape, including arch curvature, of each of the consumer's feet. The volume, length, width, and three characteristic heights of each foot are also displayed. The controller 200 uses both pressure and IR data to compute such measurements. The first height measurement is measured from the base of the leg, the last, at the front end of the height matrix, and the middle, midway between the first and the last height measurements.

Figure 15:
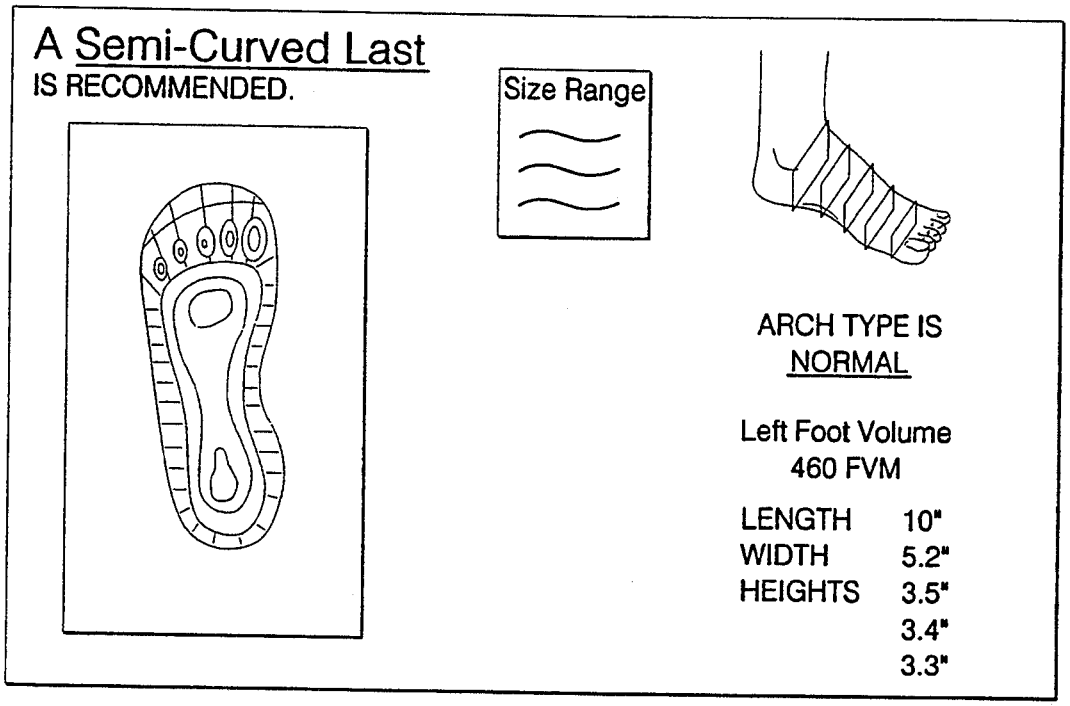
FIG. 15 is a representation of a last screen as displayed on the monitor.

FIG. 15 shows an example of an acceptable "last" screen which includes previously displayed information, along with an arch evaluation and a "last" evaluation based on pronation, and a pressure overlay of an appropriate "last." The relationships between pronation, arches, and "last" recommendations are considered understood by those reasonably skilled in the art.

Figure 16:
FIG. 16 is a representation of a best fit screen as displayed on the monitor.

FIG. 16 shows an example of a best fit data prompting screen which prompts the consumer for information relating to the anticipated surface type to be encountered, anticipated activities, correction of computed pronation, and special needs for surface or volume, including whether an arch support is normally used by the consumer.

Figure 17:
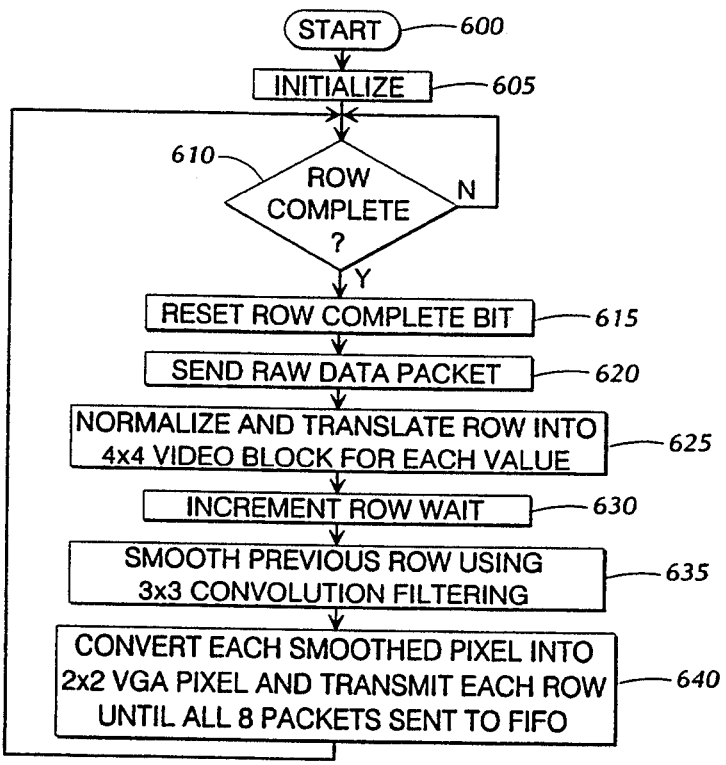
FIG. 17 is a flow chart representation of the steps taken by the foreground processes of the pressure DSP of FIG. 7.

Refer now to FIG. 17, which shows a flow chart representation of the steps taken by the foreground process of the pressure DSP 230 (FIG. 7). For convenience, refer also to FIGS. 6–8. Before the process begins at a start step 600, the controller 200 loads the DSP program memory 224 and resets the pressure DSP 230. During an initialize step 605, the pressure DSP 230 sets variables, timer interrupts, and memory speeds, and copies external variables into internal memory. After initialization, the pressure DSP 230 operates in a tight loop about step 610 which queries whether an entire row has been scanned. After a timer interrupt is set during the initialize step 605, the foreground process is continually interrupted by the timer service routine, shown in FIG. 18.

Figure 18:
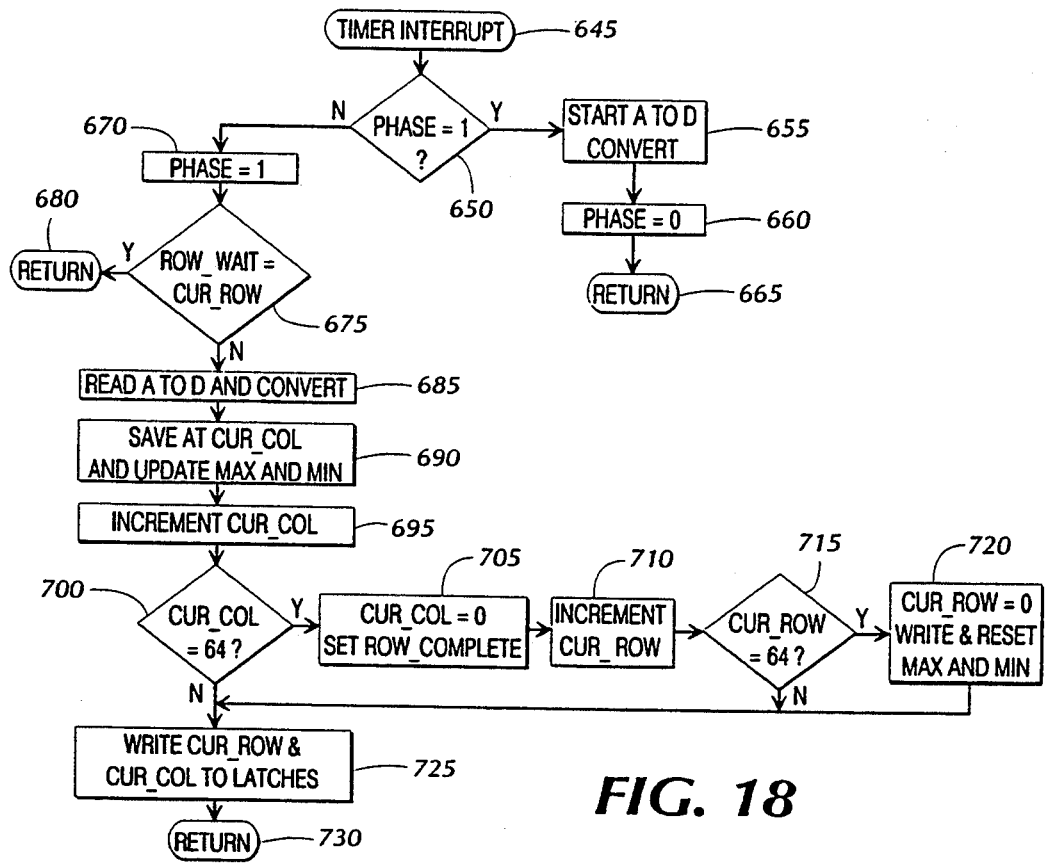
FIG. 18 is a flow chart representation of the steps taken by the timer interrupt service routine of the pressure DSP of FIG. 7.
Figure 19:
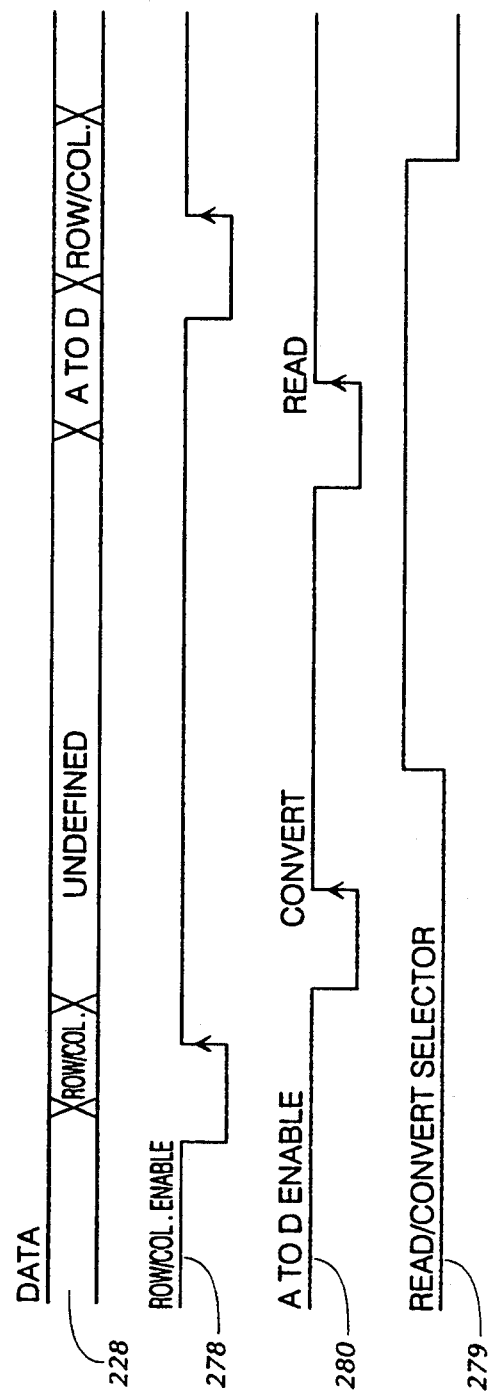
FIG. 19 is a timing diagram of signals present on the pressure sensor control and data lines of FIG. 7.
Figure 20:
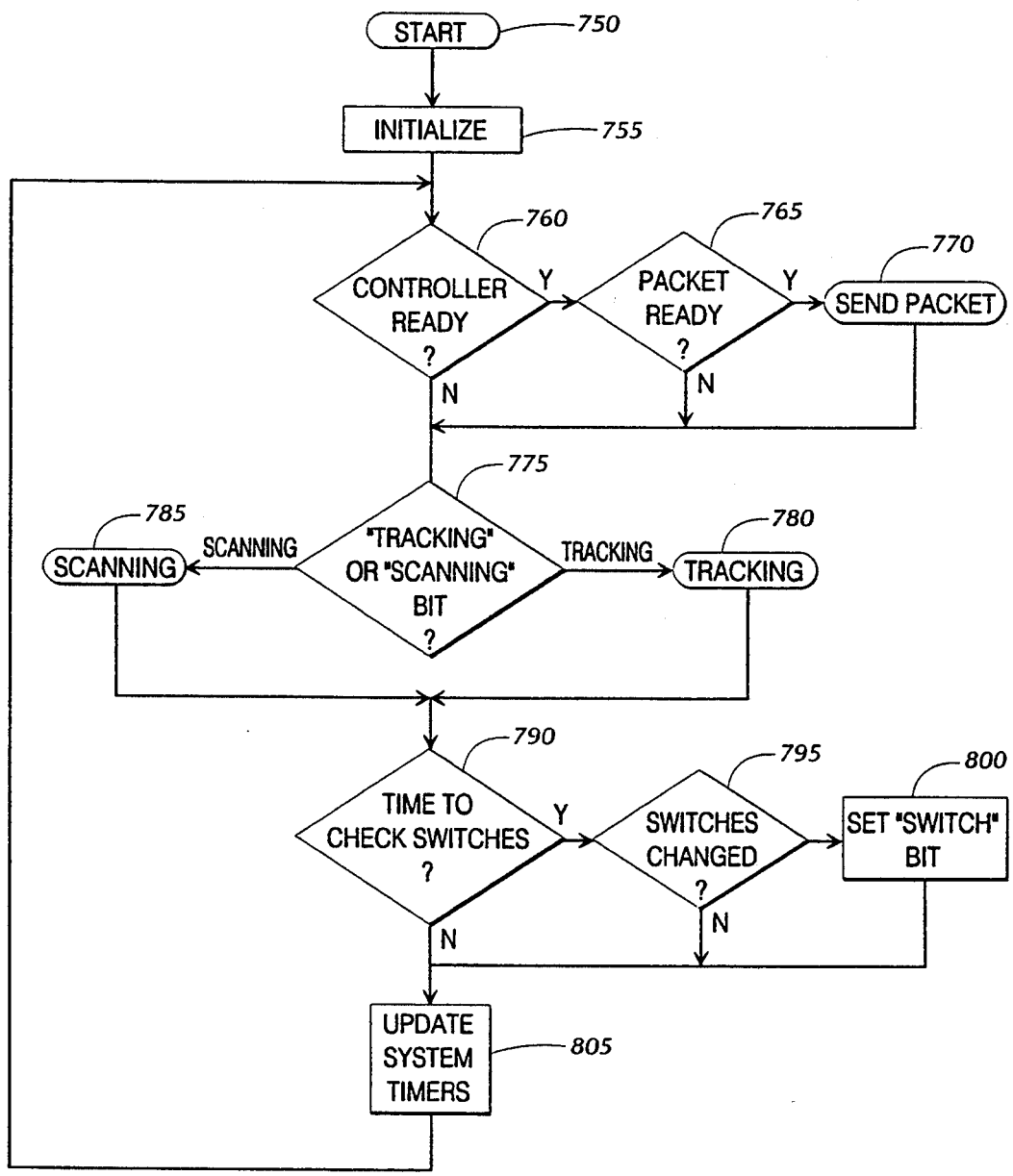
FIG. 20 is a flow chart representation of the steps taken by the control loop of the IR microprocessor of FIG. 7.

Referring also to FIGS. 18 and 19, the timer interrupt service routine 645 begins by determining whether this particular pass through the routine is a "read" pass or a "convert" pass. If a phase variable is set to 1, the Yes branch of decision block 650 is taken to step 655 which indicates that the A-to-D converter 269 is told to begin converting. This is accomplished by pulsing the A-to-D enable line 280 while the read/convert selector 279 is low. As is discussed below with respect to step 725, the current row and column selects were written to the latches 268 and 284 during the previous pass by driving the DSP data bus 228 and pulsing the row/column enable 278. After the A-to-D conversion is started, the phase variable is set to 0 at step 660, and the interrupt routine returns at step 665 to the foreground process in FIG. 17.

During the next timer interrupt, the state of the phase variable will cause control to proceed along the No branch of decision block 650 to step 670 which again sets the phase variable to 1. Subsequently at decision block 675, the variables row_wait and cur_row are checked as a pacing mechanism to prevent the foreground process from overwriting the internal data buffer. If the variables are the same, the routine returns at step 680. If not, step 685 indicates that the timer service routine causes the A-to-D converter 269 to be read and converts the data into appropriate pressure data by referencing one or more tables conversion tables in the program memory 224. The A-to-D read command includes pulsing the A-to-D enable line 280 while the read/convert selector 279 is high.

Step 690 indicates that the pressure value is then saved in the current column location (cur_col) in the data buffer and that max and min variables are updated if the present value is higher or lower, respectively. The current column location is then updated at step 695. If the current column equals 64, the row is complete, and the Yes branch of decision block 700 is taken. Step 705 indicates that the current column location is reset to zero, and the row_complete bit is set. The current row is then incremented at step 710 and evaluated at decision block 715. If the current row equals 64, the current row is reset to zero, and the max and min values are written for foreground process access and reset for interrupt purposes. Ultimately, the current row and column amounts are written to the latches 268 and 284 to scan the next pressure cell.

Referring back to FIGS. 17 and 6-8, when the foreground process sees the row_complete bit, the Yes branch of decision block 610 is taken to step 615 which resets the row_complete bit. At step 620, the pressure DSP 230 prepares and sends a raw data packet to the DSP FIFO 227 and sets a handshaking bit in the control register 226 to signal the controller 200 to read the raw data packet. At step 625, the row of pressure data is normalized and translated into four rows of video data such that each sample of pressure becomes a 4×4 matrix of identical normalized video data.

Normalization produces a more appealing color spectrum on the monitor 24 by scaling for each different consumer. The normalization process includes mapping an actual pressure reading (P) into a video range (min_v to max_v) according to the min and max of the previous scan through each contact board 60, 90 (min_p and max_p). If the pressure reading is below a certain pre-set threshold value, the video value becomes zero. Otherwise, the normalized video value is obtained by the following formula:

$$min\_v+(P-min\_p)*(max\_v-min\_v)/(max\_p-min\_p).$$

After normalization and translation, the row_wait variable is incremented at step 630.

Step 635 indicates that the pressure DSP smooths then smooths the previous four video rows (from the previous pressure row) using a 3×3 convolution filtering method, which is considered understood by those skilled in the art of smoothing. At step 640, each row of video data is then converted such that each pixel becomes a 2×2 VGA pixel matrix. Each of the eight rows are then transmitted as video packets to the DSP FIFO 227 to be read by the controller 200.

FIGS. 20-25 describe, in flow chart form, the operation of the IR system of the preferred embodiment of the present invention. For convenience, refer also to FIGS. 6 and 7. As with operation of the pressure DSP 230, the controller 200 first loads the IR RAM 238 before the start step of FIG. 20. After the process begins, the IR processor 244 initializes and queries in decision block 760 whether the controller 200 is ready to receive packets. If so, and a packet is ready to send, decision block 765, (i.e., a send_type bit is set) the process jumps to the send packet subroutine 770, discussed in detail below.

Decision block 775 indicates that "tracking " and "scanning " action bits are checked to determine whether the IR system is in tracking or scanning mode. The scanning mode is used when no feet are present in the foot wells, and the tracking mode is used when feet are present, blocking one or more optical signals. Control is then transferred to the appropriate tracking or scanning subroutines 780, 785, discussed in detail below. Decision blocks 790 and 795 indicates that the status of the switches 28 are checked periodically. If the status has changed, the "switch " bit is set in a send_type byte which identifies ready packet types. Subsequently, the system timers are updated in step 805.

Figure 21:
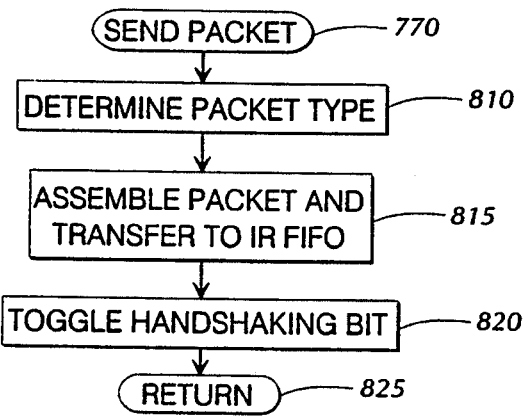
FIG. 21 is a flow chart representation of the steps taken by the send packet subroutine of the IR microprocessor of FIG. 7.

FIG. 21 shows a flow chart representation of the send packet subroutine 770. The packet type to be assembled and sent is first determined in step 810 based on the send_type byte. At step 815 the packet is assembled and transferred to the IR FIFO 236. Step 820 indicates that the handshaking bit in the control register 226 is toggled to notify the controller 200 that a packet is available. Subsequently, control is returned in step 825.

Figure 22:
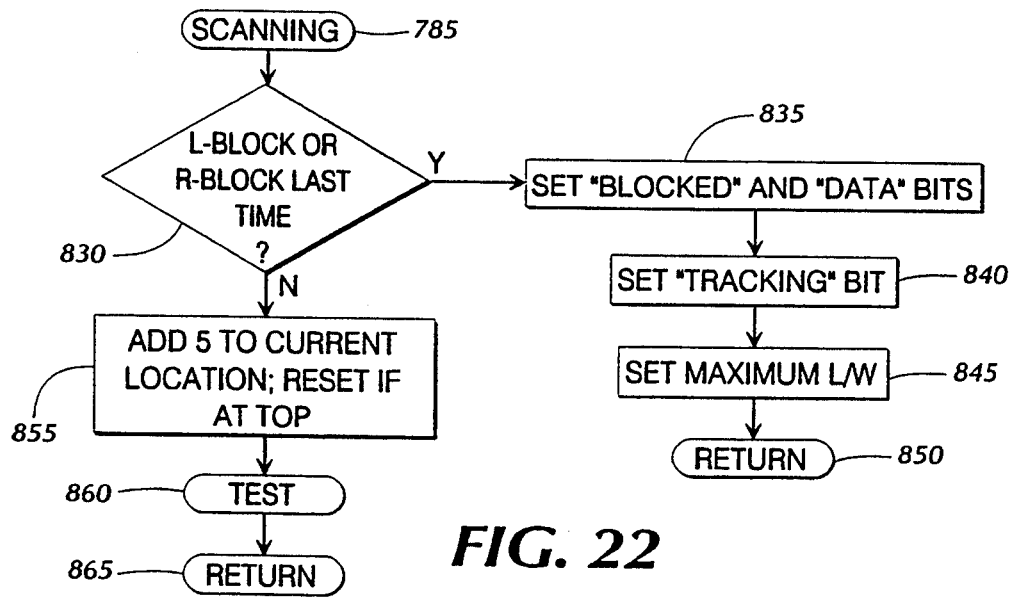
FIG. 22 is a flow chart representation of the steps taken by the scanning subroutine of the IR microprocessor of FIG. 7.

FIG. 22 is a flow chart representation of the scanning subroutine 785. According to step 830, if an l-block or r-block bit was set during the previous scan, the "blocked" and "data" send_type bits are set, as indicated by step 835. The "tracking" bit is set at step 840, and length and width variables are reset to maximum values at step 845. Control is then returned at step 850. If an l-block or r-block bit was not set during the previous scan, step 855 indicates that the current location is incremented by 5 or reset if at the end. The test subroutine 860 is then called, followed by a return at step 865.

Figure 23:
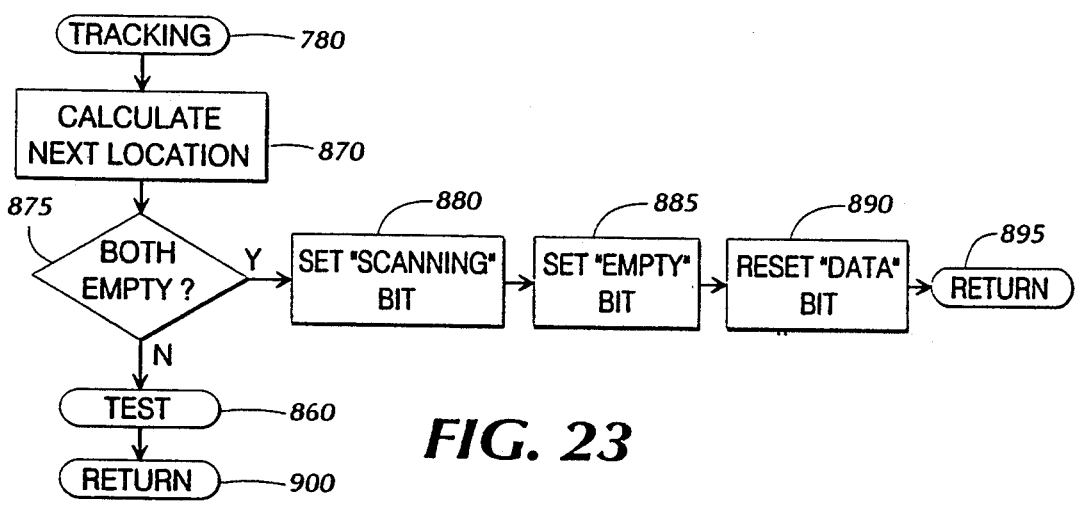
FIG. 23 is a flow chart representation of the steps taken by the tracking subroutine of the IR microprocessor of FIG. 7.

FIG. 23 shows the tracking subroutine 780 which indicates that the next location is first calculated at step 870. This step represents a "dithering" method which, with respect to one end of one line of an array, such as the length, width, or a physical height column, moves inward from the outer most boundary until encountering a blocked signal, moving backward until the signal is cleared, and again moving inward until encountering another blocked signal, thus tracking the boundary. The method rotates through the arrays and keeps track of each boundary for each array line for each foot. Upon encountering boundaries, the values are saved for placement in the data packets.

After the next locations are calculated, the tracking subroutine checks to see if both foot wells 40, 70 (FIG. 1) are empty by comparing the last calculated boundaries. If empty, the "scanning" action bit and "empty" send_type bits are set, and the "data" send_type bit is reset. Control is then returned at step 895. If not empty, the test subroutine 860 is initiated, followed by a return 900.

Figure 24:
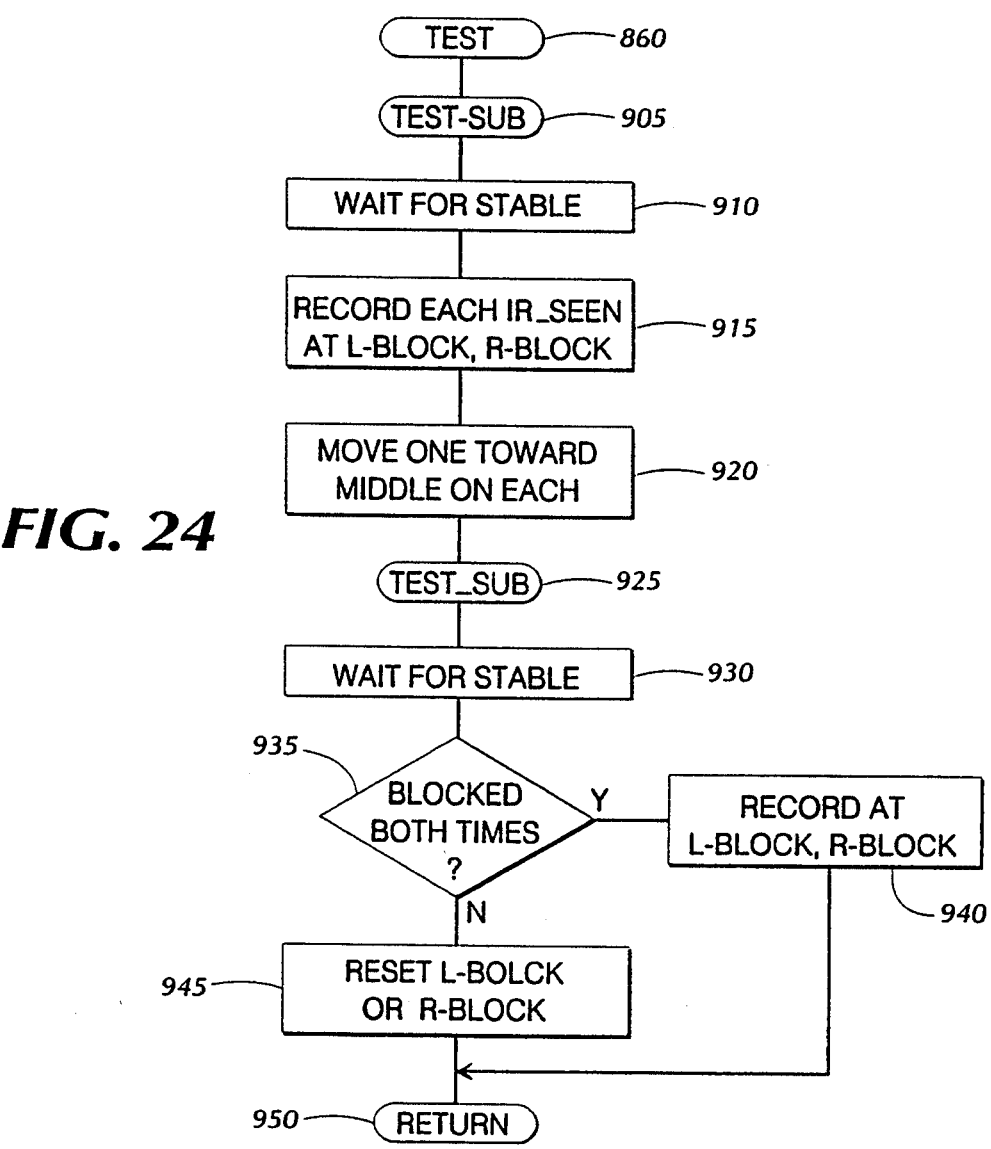
FIG. 24 is a flow chart representation of the steps taken by the test subroutine of the IR microprocessor of FIG. 7.
Figure 25:
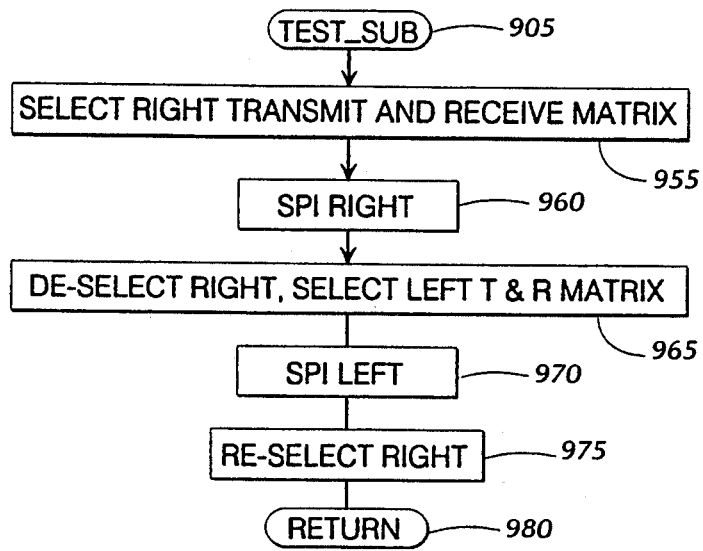
FIG. 25 is a flow chart representation of the steps taken by the test__sub subroutine of the IR microprocessor of FIG. 7.

FIG. 24 represents the test subroutine 860 and immediately calls the test_sub subroutine at step 905 which is shown in FIG. 25. According to FIG. 25, the test_sub subroutine 905 selects a right transmit and right receive matrix at step 955 and sends transmitter and receiver selection data out on the SPI data line 241 to the selected right matrix. In the preferred embodiment, corresponding transmitter and receiver are selected. However, alternate embodiments include selecting non-corresponding pairs to derive additional types of data. The right matrixes are then disabled, and the left transmit and receive matrixes are selected and sent SPI data according to steps 965 and 970. Subsequently, the right matrixes are re-selected at step 975, and control is returned to the test subroutine at step 980.

Step 910 in FIG. 10 indicates that the IR processor 244 waits for a stable signal and then records the results of each IR_seen 251, 252 at the l-block and r-block bits at step 915. The test subroutine 860 then begins a process of determining whether an actual boundary, rather than trash or an error, has been encountered. At step 920, one location closer inward is calculated for both the left and right system and tested in test_test at step 925, followed by another wait at step 930. If blocked both times, l-block or r-block are set at step 940, or reset at step 945 if not blocked both times. Control is then returned at step 950.

While the embodiments of the present invention which have been disclosed herein are the preferred forms, other embodiments of the method and apparatus of the present invention will suggest themselves to persons skilled in the art in view of this disclosure. Therefore, it will be understood that variations and modifications can be effected within the spirit and scope of the invention and that the scope of the present invention should only be limited by the claims below.

We claim:

1. A shoe fitting apparatus comprising:
   a pressure means for the generating a plurality of foot pressure signals, wherein said pressure means includes, at least, a pressure sensitive pad means for supporting a customer, said pressure sensitive pad means including, at least, a matrix of pressure sensors;
   an optical means for generating foot dimension signals including, at least, foot length, foot width, and foot height signals, wherein said optical means includes, at least,
      a first plurality of optical emitters arranged in a first linear pattern,
      a first plurality of optical receivers arranged to receive optical signals from said first plurality of optical emitters,
      a second plurality of optical emitters arranged in a second linear pattern perpendicular to said first linear pattern,
      a second plurality of optical receivers arranged to receive optical signals from said second plurality of optical emitters,
      a third plurality of optical emitters arranged in a matrix pattern located above said first and second linear patterns, and
      a third plurality of optical receivers arranged to receive optical signals from said third plurality of optical emitters; and
   a controller means for receiving said foot pressure signals and said foot dimension signals and for generating and displaying show size information.

2. An apparatus for measuring and analyzing a pair of feet, said apparatus comprising:
   a frame structure defining a left foot well and an adjacently located right foot well, said frame structure including, at least,
      a left well floor surface bounding a bottom of said left foot well,
      a right well floor surface bounding a bottom of said right foot well,
      a left well front wall surface extending perpendicularly up from said left well floor surface and bounding a front side of said left foot well,
      a right well front wall surface extending perpendicularly up from said right well floor surface and bounding a front side of said right foot well,
      a left well rear wall surface extending perpendicularly up from said left well floor surface and bounding a rear side of said left foot well,
      a right well rear wall surface extending perpendicularly up from said right well floor surface and bounding a rear side of said right foot well,
      a left well outer wall surface extending perpendicularly up from said left well floor surface and bounding an outer side of said left foot well,
      a right well outer wall surface extending perpendicularly up from said right well floor surface and bounding an outer side of said right foot well,
      a left well inner wall surface extending perpendicularly up from said left well floor surface and bounding an inner side of said left foot well, and
      a right well inner wall surface extending perpendicularly up from said right well floor surface and bounding an inner side of said right foot well;
   a pressure system connected to said frame structure including, at least,
      a plurality of pressure sensors including, at least,
         a left well matrix of pressure sensors including, at least,
            a left well contact layer including, at least, a plurality of open sensor contacts arranged as a planar matrix covering said left well floor surface, and
            a left well pressure-sensitive, variably resistive layer covering said left well contact layer,
         a right well matrix of pressure sensors including, at least,
            a right well contact layer including, at least, a plurality of open sensor contacts arranged as a planar matrix covering said right well floor surface, and
            a right well pressure-sensitive, variably resistive layer covering said right well contact layer,
      a voltage supply means for continually supplying voltage to at least one pressure sensor of said plurality of pressure sensors,
      a current detection means for continually and sequentially detecting current flowing through each pressure sensor of said plurality of pressure sensors and for generating output signals representative of current flowing through each pressure sensor of said plurality of pressure sensors, and
      a pressure processing means coupled to said voltage supply means and said current detection means for controlling the continual and sequential operation of said plurality of pressure sensors and continually converting said output signals from said current detection means into pressure data representative of pressure applied to said plurality of pressure sensors;
   an optical system connected to said frame structure including, at least,
      a left well length plurality of optical emitters extending along one of said left well inner wall surface and said left well outer wall surface, an opposing left well length plurality of optical receivers extending along the other of said left well inner wall surface and said left well outer wall surface,
      a left well height plurality of optical emitters extending up one of said left well inner wall surface and said left well outer wall surface, an opposing left well height plurality of optical receivers extending up the other of said left well inner wall surface and said left well outer wall surface,
      a left well width plurality of optical emitters extending along one of said left well front wall surface and said left well rear wall surface, an opposing left well width plurality of optical receivers extending along the other of said left well front wall surface and said left well rear wall surface,
      a right well length plurality of optical emitters extending along one of said right well inner wall surface and said right well outer wall surface, an opposing right well length plurality of optical receivers extending along the other of said right well inner wall surface and said right well outer wall surface, a right well height plurality of optical emitters extending up one of said right well inner wall surface and said right well outer wall surface, an opposing right well height plurality of optical receivers extending up the other of said right well inner wall surface and said right well outer wall surface, a right well width plurality of optical emitters extending along one of said right well front wall surface and said right well rear wall surface, an opposing right well width plurality of optical receivers extending along the other of said right well front wall surface and said right well rear wall surface, and an optical processing means coupled to said pluralities of optical emitters and receivers for controllably causing said pluralities of optical emitters to emit optical signals and causing said pluralities of receivers to generate electrical signals representative of optical signals received by said pluralities of optical emitters, and for generating, based on said electrical signals received from said pluralities of optical receivers, optical data representative of detected edges of any feet substantially randomly located within said left well and said right well, said detected edges including a left well outer edge, a left well inner edge, a left well front edge, a left well rear edge, a left well upper edge, a right well outer edge, a right well inner edge, a right well front edge, a right well rear edge, and a right well upper edge; and a controller connected to said frame structure and coupled to said pressure processing means and said optical processing means, said controller including, at least, a controller processor means for receiving said pressure data from said pressure processing means and said optical data from said optical processing means and for calculating foot measurement data including, at least, length, width, height, and volume data for left and right feet based at least upon said optical data from said optical processing means, and a graphical display means coupled to said controller processor means for displaying portions of said foot measurement data and said pressure data.

3. The apparatus of claim 2, wherein said controller processor means includes, at least, adjustment means for accommodating angled feet by utilizing said pressure data to adjust said foot measurement data to calculate adjusted length and adjusted width data.

4. The apparatus of claim 3, wherein said adjustment means includes, at least, means for calculating foot angle data based upon said pressure data.

5. The apparatus of claim 2, wherein said pressure processing means further includes, at least, video normalizing means for generating normalized pressure video data for input directly to said graphical display means.

6. The apparatus of claim 2, wherein said optical processing means further includes, at least, tracking means for continually dithering back and forth around detected edges.

7. The apparatus of claim 2, wherein said controller processor means utilizes said length, width, height, and volume data to calculate a shoe size for each foot within said left and right wells.

8. An apparatus for measuring at least one foot, said apparatus comprising:

a plurality of optical sensors arranged to define a sensing area for receipt of a foot;

an optical directing means for causing said plurality of optical sensors to employ optical signals to locate front, rear, left, and right edges of a foot substantially randomly located within said sensing area and for generating optical data representing located edges of the foot; and a controller means for receiving said optical data and for calculating and displaying foot measurement data including, at least, length and width data, wherein said plurality of optical sensors includes, at least, a matrix of vertically arranged optical sensors, and wherein said optical directing means causes said matrix of sensors to employ optical signals to locate, at least, a first height of a foot at a base of a leg and a second height of a foot at a second location nearer front of the foot.

* * * * *